(12) United States Patent
Malecki

(10) Patent No.: US 7,852,282 B2
(45) Date of Patent: Dec. 14, 2010

(54) SYSTEM AND METHOD FOR EXCLUDING ELECTROMAGNETIC WAVES FROM A PROTECTED REGION

(76) Inventor: Zbigniew Malecki, 108 Devonglen Dr., Kitchener (CA) N2E 2C5

( * ) Notice: Subject to any disclaimer, the term of this patent is extended or adjusted under 35 U.S.C. 154(b) by 377 days.

(21) Appl. No.: 12/096,980

(22) PCT Filed: Dec. 13, 2006

(86) PCT No.: PCT/CA2006/002027
§ 371 (c)(1),
(2), (4) Date: Jun. 11, 2008

(87) PCT Pub. No.: WO2007/068108
PCT Pub. Date: Jun. 21, 2007

(65) Prior Publication Data
US 2009/0001297 A1 Jan. 1, 2009

Related U.S. Application Data

(60) Provisional application No. 60/749,623, filed on Dec. 13, 2005.

(51) Int. Cl.
H01Q 1/36 (2006.01)
(52) U.S. Cl. .................. 343/895; 343/796; 343/801
(58) Field of Classification Search .............. 343/895, 343/793, 795, 796, 801, 810
See application file for complete search history.

(56) References Cited

U.S. PATENT DOCUMENTS

| | | | |
|---|---|---|---|
| 3,608,280 A | 9/1971 | Martin | |
| 4,703,133 A | 10/1987 | Miller | |
| 4,801,807 A | 1/1989 | Jacobs | |
| 5,122,332 A | 6/1992 | Russell | |
| 5,153,378 A | 10/1992 | Garvy, Jr. | |
| 5,616,928 A | 4/1997 | Russell et al. | |
| 5,761,053 A | 6/1998 | King et al. | |
| 6,249,006 B1 | 6/2001 | Sakiyama | |
| 6,320,124 B1 | 11/2001 | Cheng | |
| 6,646,198 B2 | 11/2003 | Maciver et al. | |
| 6,992,314 B2 | 1/2006 | Masaki et al. | |
| 2002/0011189 A1 | 1/2002 | Leightner et al. | |
| 2004/0011972 A1 | 1/2004 | Alishahi | |
| 2006/0255945 A1* | 11/2006 | Egbert | 340/572.7 |
| 2008/0316124 A1* | 12/2008 | Hook | 343/705 |
| 2009/0011922 A1* | 1/2009 | de Rochemont | 501/137 |

FOREIGN PATENT DOCUMENTS

WO PCT/CA2006/002027 6/2007

* cited by examiner

*Primary Examiner*—HoangAnh T Le

(57) ABSTRACT

A module for receiving one or more electromagnetic waves moving along a path in a direction of propagation. The module includes a first electrically conductive strip disposed in a first pattern and a second substantially electrically conductive strip disposed in a second pattern. The first and second strips are positioned substantially parallel to each other and spaced apart, and are electrically connected to each other. The first and second patterns are substantially opposite to each other, so that current passing through the first and second strips generates respective electromagnetic fields which are substantially opposed to each other. The first strip is positionable in the path of the electromagnetic wave and substantially transverse to the direction of propagation, to provide a protected region from which said at least one electromagnetic wave is substantially excluded.

18 Claims, 19 Drawing Sheets

SYSTEM AND METHOD FOR EXCLUDING ELECTROMAGNETIC WAVES FROM A PROTECTED REGION

FIELD OF THE INVENTION

The present invention is related to a module for receiving electromagnetic waves.

BACKGROUND OF THE INVENTION

Electromagnetic waves are generally thought to have an adverse effect on the health of human beings, or at least the potential to cause such an adverse effect. Electromagnetic waves emanating from electric power transmission lines or transformers have been found to adversely affect the health of human beings, although the mechanism whereby electromagnetic waves adversely affect the human body is not well understood.

Electromagnetic waves are natural or man-made. Very high-frequency electromagnetic waves have been shown to emanate from the Earth. The original source, or cause, of these electromagnetic waves has not been identified. However, this electromagnetic radiation does appear to result from natural causes. It appears that these high-frequency electromagnetic waves typically are directed in a direction which is substantially orthogonal to the Earth's surface, if there is nothing present in the Earth's crust to disturb the electromagnetic waves. However, these electromagnetic waves appear to be affected by different materials (e.g., underground running water, or cavities, or certain types of mineral deposits), which can distort or disturb the electromagnetic waves (as shown in FIGS. 1A and 1B). These disturbed and/or distorted parts of the electromagnetic waves (collectively hereinafter referred to as "streams of distorted high-frequency electromagnetic radiation") are of particular concern because they appear to have an adverse effect upon the human body, as will be described.

The streams of distorted high-frequency electromagnetic radiation are parts of very high-frequency electromagnetic waves (e.g., approximately 150 GHz or greater), and they appear to be relatively widespread. Typical structures (e.g., houses, or office buildings) are substantially transparent to these electromagnetic waves. This is in contrast to, for example, the shielding effect a structure can exhibit relative to a low-frequency electromagnetic wave.

The streams of distorted high-frequency electromagnetic radiation also appear generally to be characterized by generally small wavelengths (e.g., microwaves or nanowaves). However, as these streams of distorted electromagnetic radiation can also be modulated by longer-wavelength electromagnetic waves, it is possible that these streams can be characterized by somewhat longer wavelengths in these circumstances.

As is well known, the Earth has a magnetic field operational between the north pole and the south pole. However, as the lines of magnetic force are virtually parallel to the Earth's surface, these streams of high-frequency electromagnetic waves do not appear to be directly related to the Earth's magnetic field.

FIG. 1A shows an underground anomaly 10 which disturbs the electromagnetic waves 11 to produce streams of distorted high-frequency electromagnetic radiation 12, 13, and 14. The strength, or intensity, of each of the streams 12, 14 generally appears to be approximately one-third of the intensity of the stream 13. Also, each of the streams 12, 14 has a path 15, 16 respectively deviating from a path 17 of the stream 13 by approximately 45°.

As can be seen in FIG. 1A, the electromagnetic waves 11 apparently move generally outwardly from the Earth's center, in the direction indicated by arrow "A". The streams 12, 13, and 14 have well-defined edges, or sides, which appear to be related to the extent of the anomaly 10. For example, as shown in FIG. 1A, the stream 12 has sides 18, 19; the stream 13 has sides 21, 23; and the stream 14 has sides 25, 27. The path 17 of the stream 13 is substantially orthogonal to the Earth's surface 29. A schematic diagram showing the manner in which the electromagnetic waves 11 are thought to emanate in a direction radially outward from the Earth's center until disturbed is provided in FIG. 1B.

FIG. 1C provides an isometric view in which the streams 12, 13, and 14 are shown. In FIG. 1D, the significance of the directions of the streams 12, 13, and 14 can be seen. A structure 33 is shown in FIG. 1D which is located substantially on or at the Earth's surface 29. In this example, the stream 12 is shown to pass through the structure 33 at different levels.

As can be seen in FIGS. 1C and 1D, the streams 12, 13 and 14 are three-dimensional regions which are downstream (i.e., relative to the electromagnetic radiation 11) from the anomaly 10. In these streams 12, 13, and 14, the electromagnetic radiation 11 appears to be distorted, relative to the electromagnetic radiation 11 upstream from the anomaly 10. Accordingly, electromagnetic fields which are also distorted are created by these streams of distorted electromagnetic radiation. The distortions apparently are caused by the anomaly 10.

It will also be understood that, for illustration, only one anomaly 10 has been shown. However, in many cases, there are a number of streams passing through the structure. For example, FIG. 1E shows a house plan (for one level of a house 35) in which a large number of streams of distorted high-frequency electromagnetic radiation 37 are present. FIG. 1E shows the intersection of the streams 37 with the floor of the house 35. (For clarity of illustration, element numbers for only a few of the streams 37 are provided in FIG. 1E. The numbers in circles in FIG. 1E represent different intensities based on a scale 41 provided in FIG. 1E.) It is thought that, where several streams of distorted electromagnetic fields are present, they are due to a number of anomalies in the Earth's crust in the vicinity of the house. Typically, the streams appear to have different intensities, for example, as indicated by the numbers in circles in FIG. 1E.

In summary, and as can be seen in FIG. 1E, the streams of distorted electromagnetic radiation appear to be very sharply-defined, in contrast to the typically somewhat ill-defined boundaries of electromagnetic fields generally. Also, each stream appears to have a path in a clearly-defined direction. This indicates that the streams are the result of a distorting, or disturbing, obstacle (i.e., an anomaly) which acts to distort the electromagnetic radiation in a fashion similar to a stone in a stream, to create a downstream zone shadowing the obstacle, in which the wave patterns are disturbed. However, it will be understood that the foregoing is only a plausible description of natural phenomena in respect of which more research is required.

In "An Evaluation of the Possible Risks from Electric and Magnetic Fields (EMFs) from Power Lines, Internal Wiring, Electrical Occupations, and Appliances" (Final Report, June 2002), the California EMF Program (California Electric Magnetic Fields Program, a project of the California Department of Health Services and the Public Health Institute) concluded:

1. that man-made electromagnetic fields can be harmful to the human body; and
2. that exposures of 2-16 milligauss are substantially equally harmful.

The Final Report is available at:
www.dhs.ca.gov/ps/deode/ehib/emf/RiskEvaluation/riskeval.html.

FIG. 1F is a graph 45 showing the California EMF Program's conclusions regarding the probabilities of certain illnesses occurring due to man-made electromagnetic radiation.

As illustrated schematically in FIG. 2, power lines 43 emanate streams 45 of man-made electromagnetic radiation. The Final Report indicates that such streams 45 are, or at least can be, harmful to humans. Also, as schematically shown in FIG. 3, a number of abnormal electromagnetic fields 47 are generated in connection with the supply of electricity to residences 49 (and to commercial premises), which abnormal electromagnetic fields may have adverse effects upon the health of those living in the residences.

As is known, an electromagnetic wave traveling in free space in a direction of propagation has an electric field component ("E") and a magnetic field component ("H") (FIG. 4). As shown in FIG. 4, the electric field component and the magnetic field component are generally perpendicular (or substantially perpendicular) to each other, and they are usually also perpendicular (or substantially perpendicular) to the direction of propagation.

As noted above, a mechanistic explanation of the effects of the streams of distorted high-frequency electromagnetic waves has not been developed. One possible explanation for the apparently harmful effects of man-made electromagnetic radiation is that the human body's immune system is activated to resist such radiation because it is inconsistent with the electromagnetic radiation which the immune system recognizes as normal.

Similarly, it is possible that the distortion of the electromagnetic radiation apparently caused by anomalies in the Earth is, like man-made electromagnetic radiation, identified by the immune system as foreign. According to this theory, the human body's immune system reacts to the distortions in the electromagnetic radiation by activating itself, i.e., the immune system recognizes distorted high-frequency electromagnetic radiation as anomalous, i.e., a "foreign" influence inside the body, and therefore is activated to defend against this potentially harmful "intruder".

If the foregoing is accurate, then the distortions in the streams of distorted electromagnetic radiation have an effect on the immune system which is very much like the effect of man-made electromagnetic fields. The distortions of high-frequency electromagnetic radiation result in stress on the immune system because the distortions differ from the typical, natural electromagnetic radiation which, due to evolution over many years, does not cause activation of the immune system. According to this theory, it is the distortions of the electromagnetic radiation, rather than the electromagnetic radiation itself, which is harmful, or potentially harmful.

Activation of the immune system appears to be substantially constant while a subject is in a distorted high-frequency electromagnetic field, and frequent and repeated exposure apparently tends to have a cumulative effect. Ultimately, this stress can result in the immune system becoming less able to respond to other threats, such as infections or other foreign agents which cause illness. Because of the weakening of the immune system, the subject's body is more seriously affected by illnesses which it might otherwise be able to resist.

There is therefore a need for a device which overcomes or mitigates one or more of the disadvantages of the prior art.

SUMMARY OF THE INVENTION

In its broad aspects, the invention provides a module for receiving one or more electromagnetic waves moving along a path in a direction of propagation. The module includes a first substantially electrically conductive strip extending between a first end and a second end thereof disposed in a first pattern substantially in a first plane, and a second substantially electrically conductive strip extending between a first end and a second end thereof disposed in a second pattern substantially in a second plane. The first and second strips are electrically connected to each other by a connector. The first and second strips are positioned substantially parallel to each other and spaced apart by a predetermined distance. Also, the first and second patterns are substantially opposite to each other, so that current passing through the first and second strips generates respective electromagnetic fields which are substantially opposed to each other. The first strip is positionable in the path of the electromagnetic wave and substantially transverse to the direction of propagation, to provide a protected region from which said at least one electromagnetic wave is substantially excluded. The protected region extends from the second strip and substantially away from the first strip.

In another aspect, the current through the first and second strips is generated by energy in the electromagnetic wave.

In yet another aspect, the first strip defines a first path direction from the first end to the second end thereof, and the second strip defines a second path direction from the first end to the second end thereof. The first path direction and second path direction are substantially opposite, so that electromagnetic fields generated by the current in said first and second strips are substantially mutually opposed.

In another of its aspects, the electromagnetic wave is at least partially converted by the first and second strips into a pulsating magnetic field released outwardly therefrom and including magnetic pulses which are directed substantially orthogonally to the first and second strips.

In another aspect, the invention provides a system for receiving a number of electromagnetic waves moving along paths in directions of propagation respectively. The system includes two or more modules. Each of the modules is positioned substantially orthogonally to each other, for combining the protected regions associated therewith respectively to define an assembly of protected regions from which the electromagnetic waves are substantially excluded.

In yet another aspect, the system includes three modules, and each of the modules is positioned substantially orthogonally to the other two modules. The three modules provide a substantially spherical assembly of protected regions from which the electromagnetic waves are substantially excluded.

In another of its aspects, the electromagnetic waves are at least partially converted by the first and second strips in each module into a pulsating magnetic field released outwardly from the first and second strips in each of the modules respectively. Each of the pulsating magnetic fields includes magnetic pulses which are directed substantially orthogonally to the first and second strips in each module respectively.

In another aspect, the invention provides a module for receiving a number of electromagnetic waves moving in a number of paths substantially in one or more directions of propagation. The electromagnetic waves have a plurality of frequencies respectively. The module includes a first substantially electrically conductive strip extending between a first end and a second end thereof disposed in a first pattern substantially in a first plane positioned substantially transverse to the direction of propagation and in the paths of the electromagnetic waves. The module also includes a second strip extending between a first end and a second end thereof disposed in a second pattern substantially in a second plane. The first and second strips are positioned substantially parallel to each other and spaced apart by a predetermined distance, and the first and second strips are electrically connected to each other. Each of the first and second strips includes a number of dipole antenna-like segments. Each dipole antenna-like segment respectively is adapted to resonate at a predetermined frequency, so that the electromagnetic waves are at least partially received at the dipole antenna-like segments and converted into current through the first and second strips which generates electromagnetic fields to provide a protected region extending from the second strip substantially away from the first strip. The electromagnetic waves are substantially excluded from said protected region.

In yet another aspect, the electromagnetic waves are at least partially converted by the first and second strips into one or more pulsating magnetic fields released outwardly therefrom including magnetic pulses which are directed substantially orthogonally to the first and second strips.

In another of its aspects, the invention provides a system for receiving a number of electromagnetic waves moving along respective paths in directions of propagation respectively. The system includes two or more modules. Each of the modules is positioned substantially orthogonally to each other module, for combining the protected regions associated therewith respectively to define an assembly of protected regions from which the electromagnetic waves are substantially excluded.

BRIEF DESCRIPTION OF THE DRAWINGS

The invention will be better understood with reference to the drawings, in which.

DETAILED DESCRIPTION

Figure 1A:
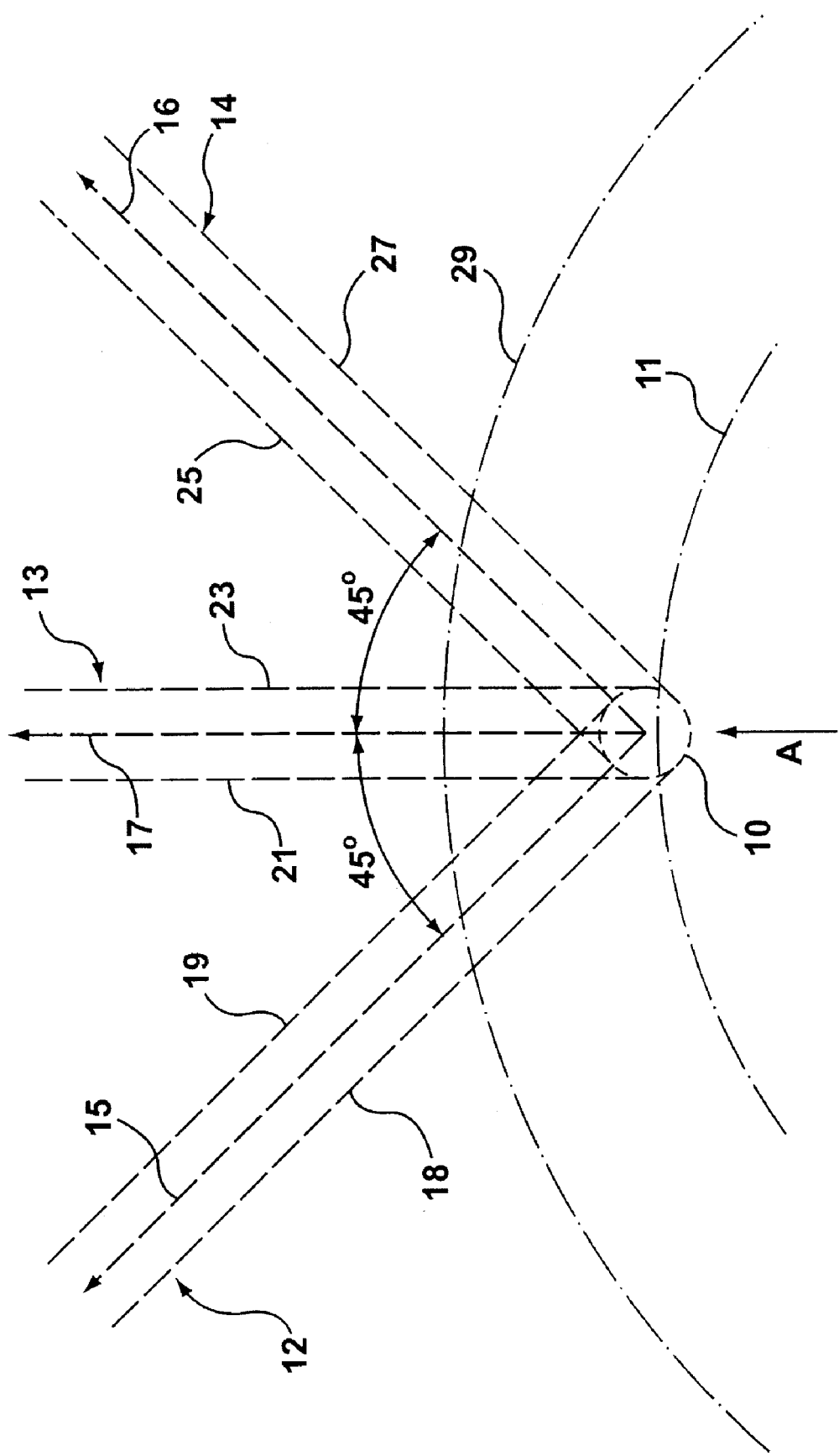
FIG. 1A (previously described) is a schematic diagram showing streams of distorted high-frequency electromagnetic radiation.
Figure 1B:
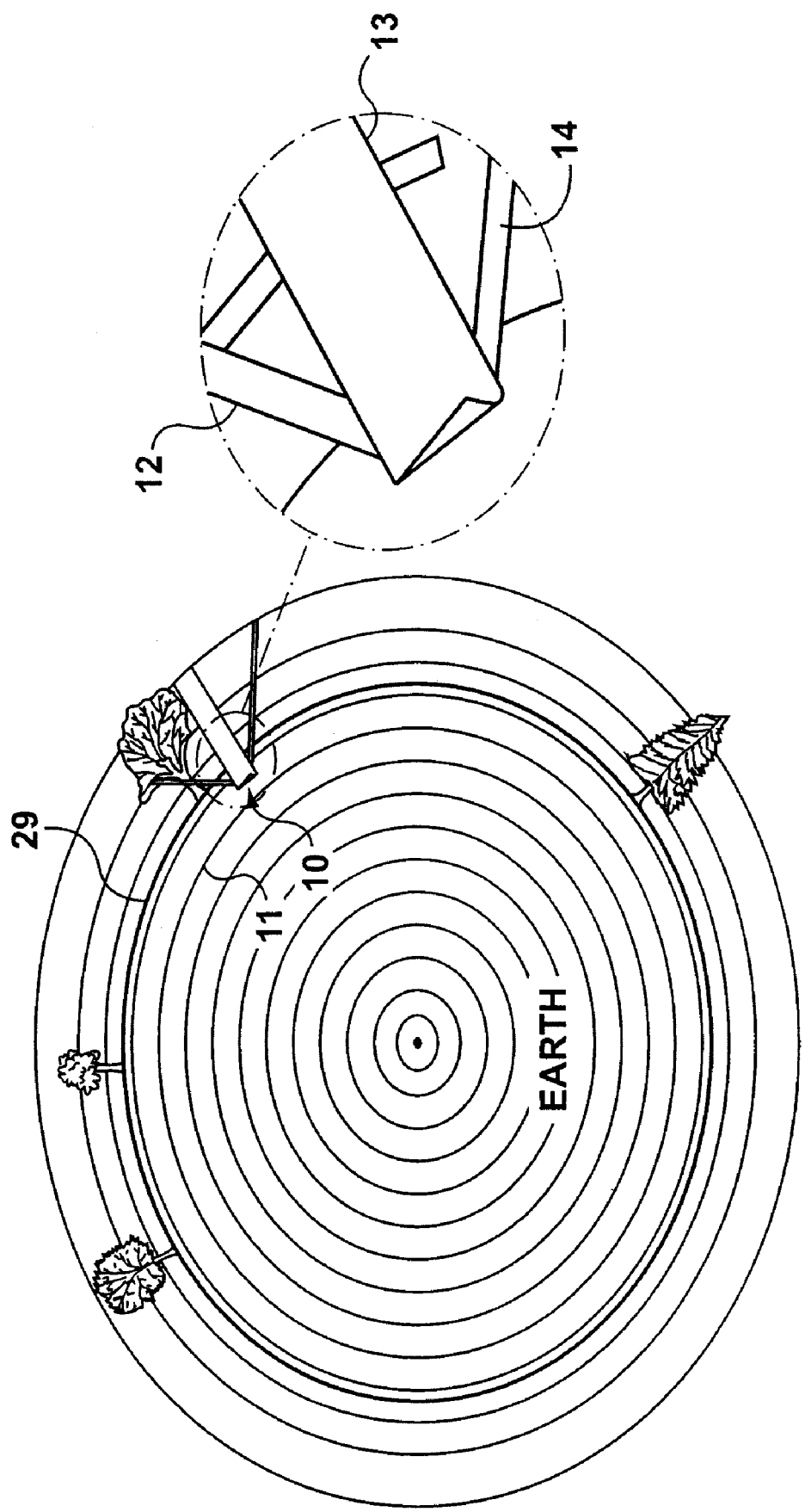
FIG. 1B (also previously described) is a schematic diagram showing a possible mechanism for the generation of electromagnetic radiation and the creation of streams of distorted high-frequency electromagnetic radiation, drawn at a smaller scale.
Figure 1C:
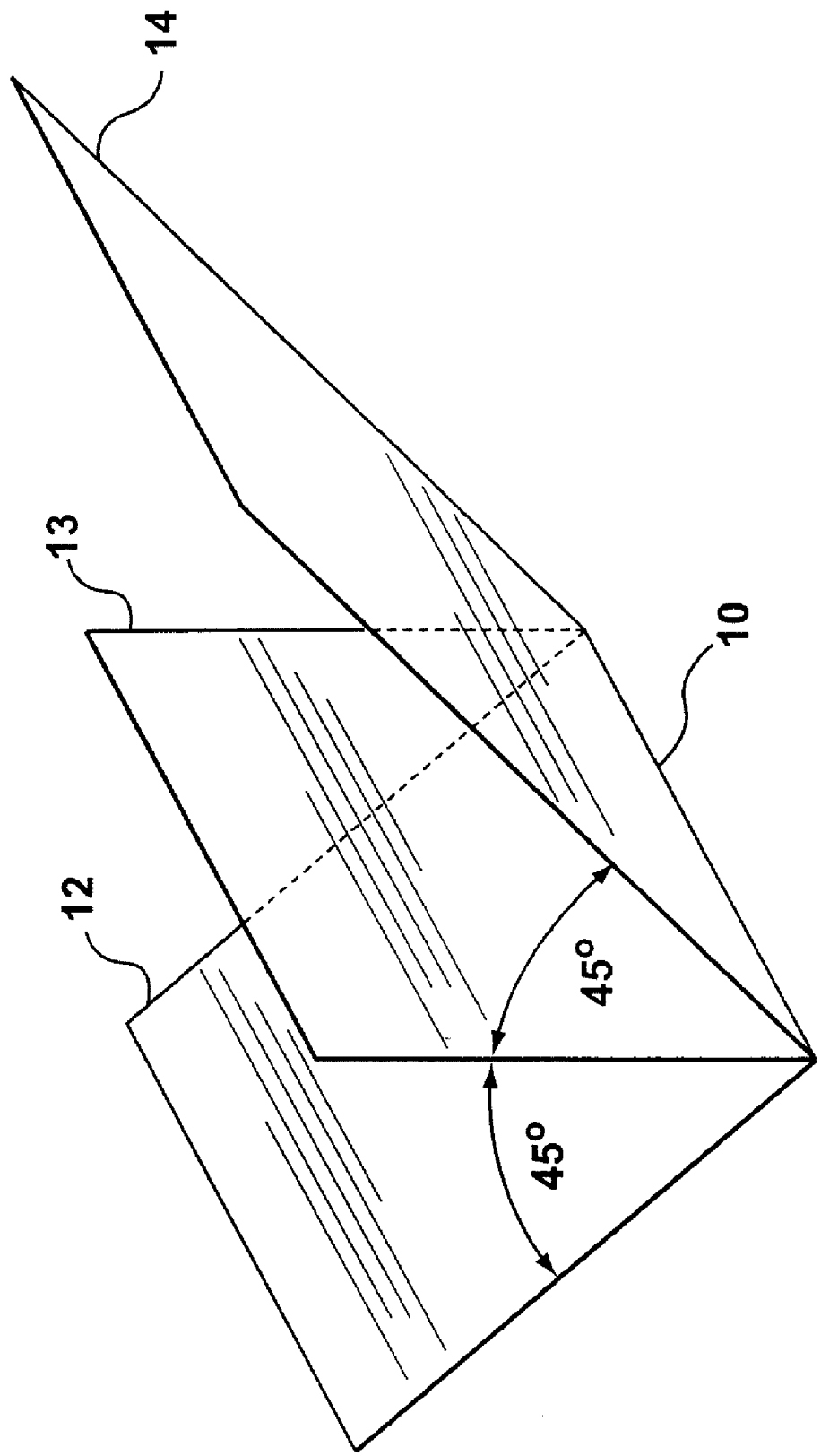
FIG. 1C (also previously described) is a schematic diagram of streams of distorted high-frequency electromagnetic radiation caused by an anomaly, drawn at a larger scale.
Figure 1D:
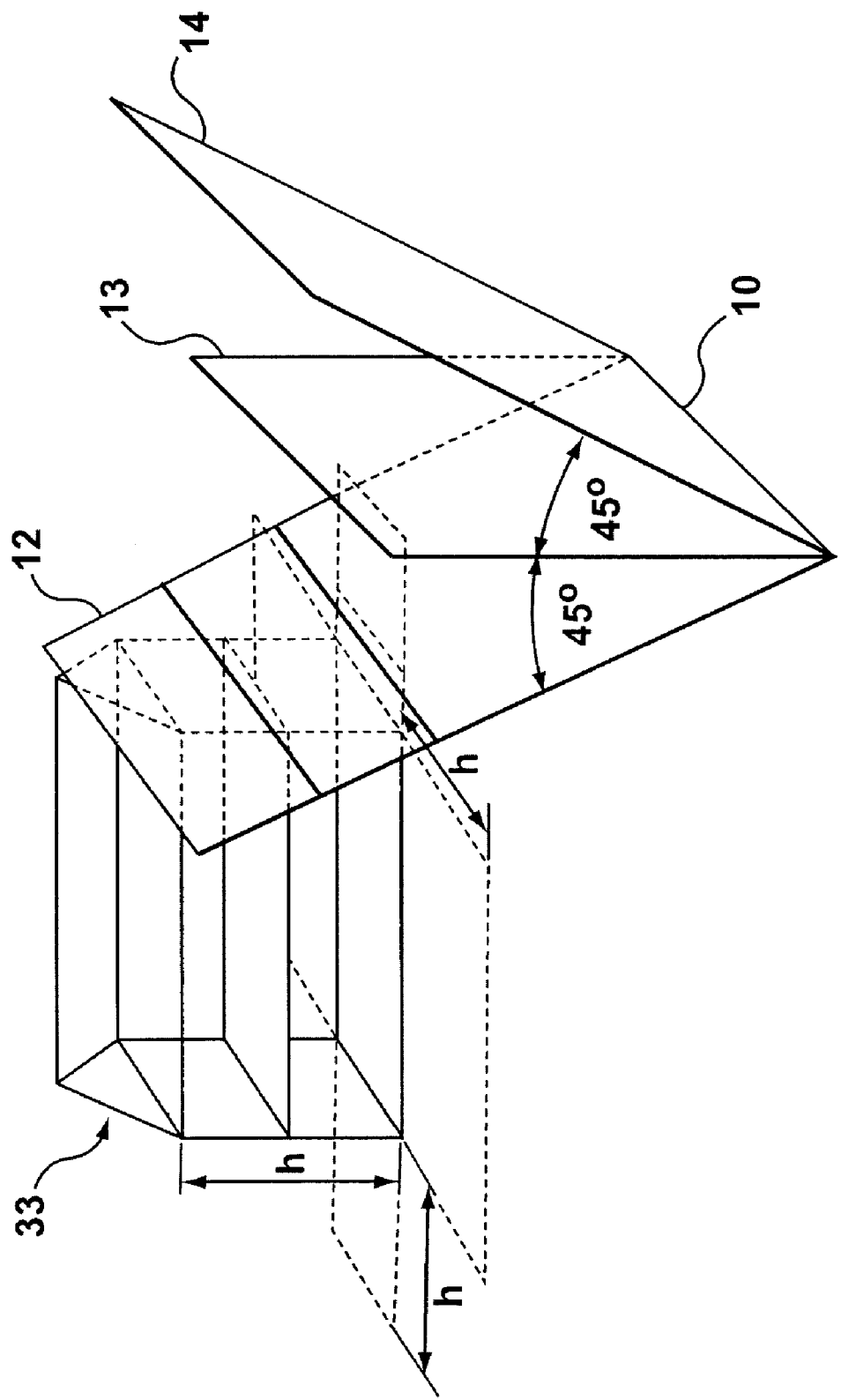
FIG. 1D (also previously described) is a schematic diagram of streams of distorted high-frequency electromagnetic radiation positioned near a structure.
Figure 1E:
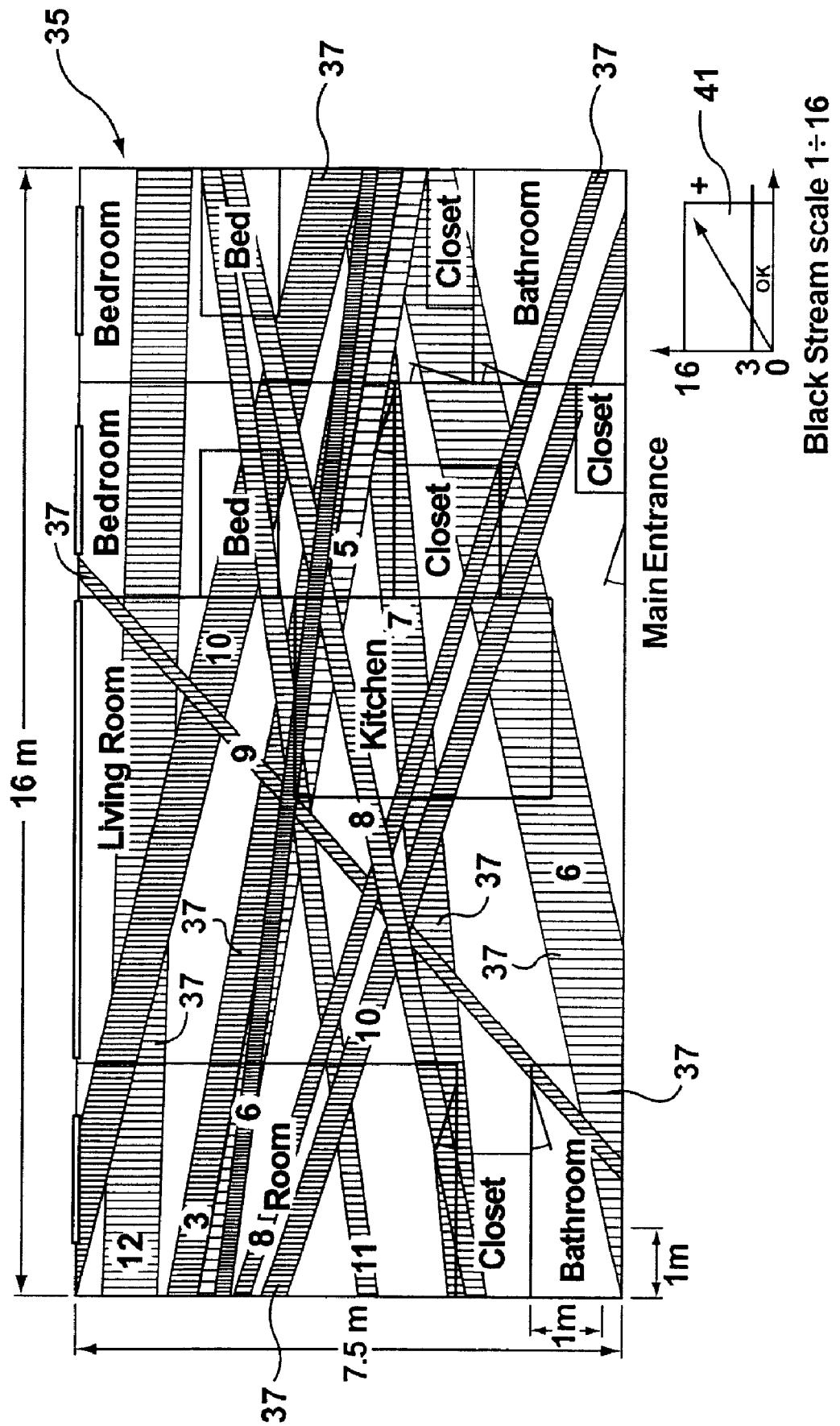
FIG. 1E (also previously described) is a plan view of a house showing electromagnetic fields resulting from streams of distorted high-frequency electromagnetic radiation.
Figure 1F:
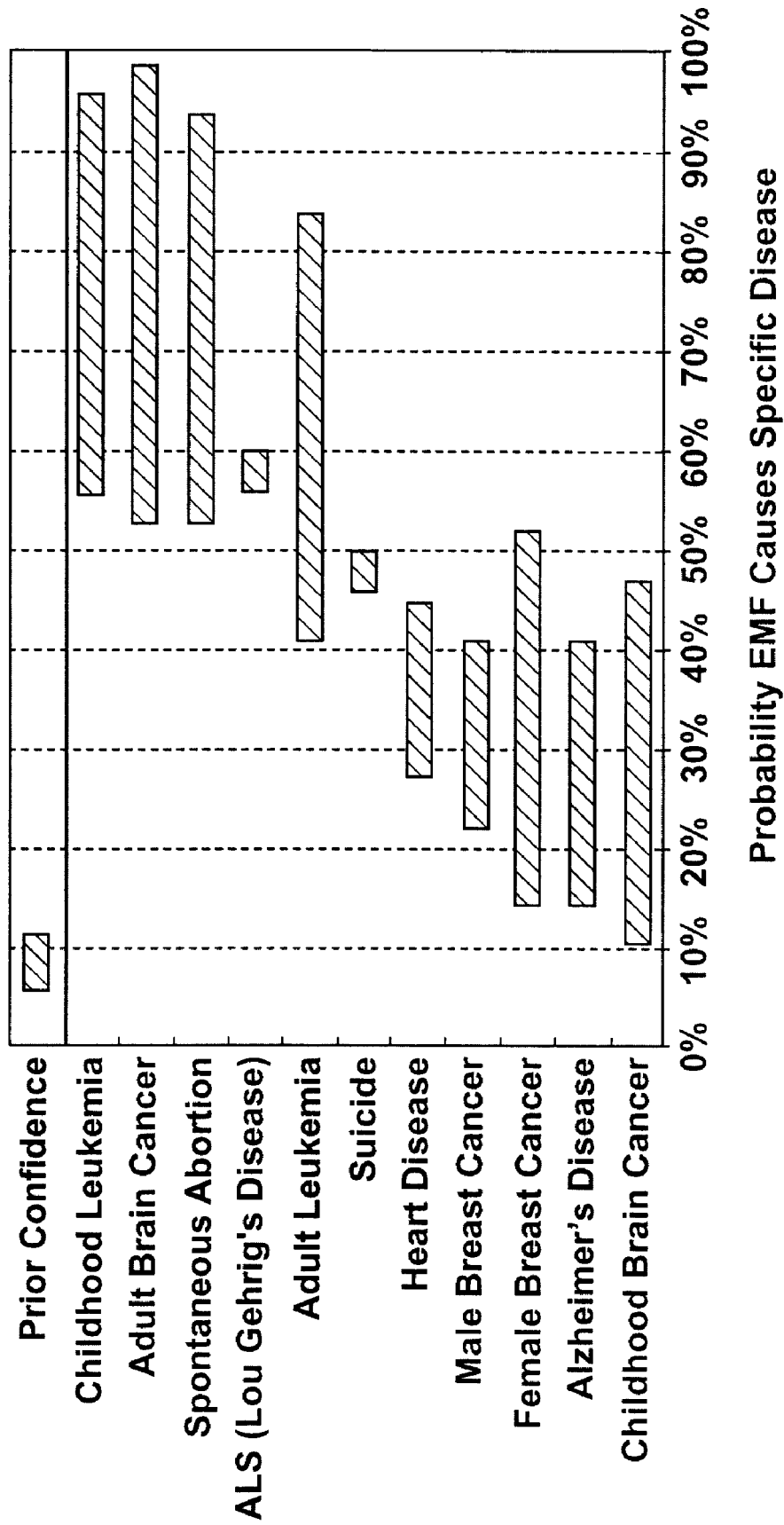
FIG. 1F (also previously described) is a graph showing estimated probabilities that man-made electromagnetic fields cause certain diseases.
Figure 2:
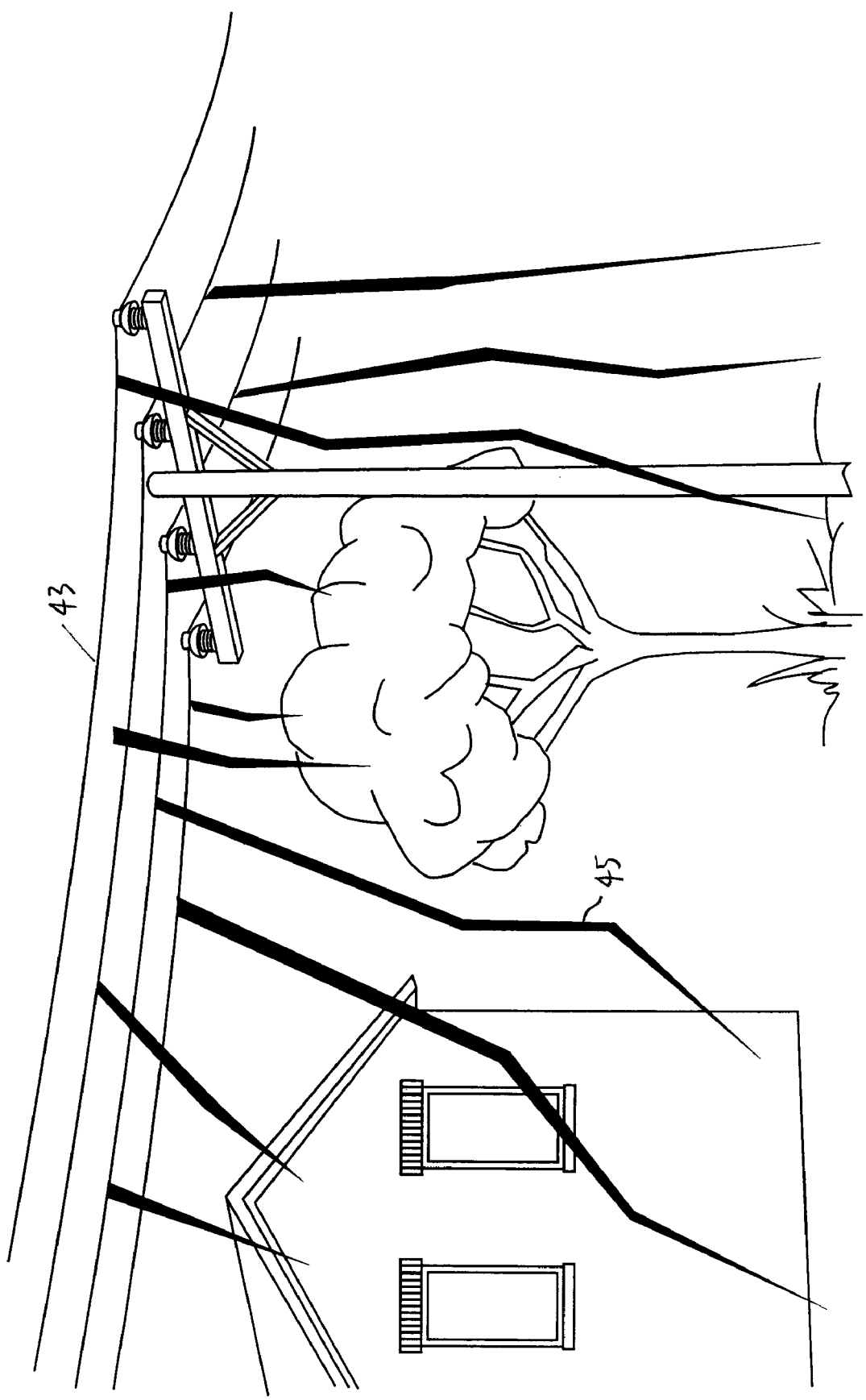
FIG. 2 (also previously described) is a schematic illustration showing man-made electromagnetic waves from a power line.
Figure 3:
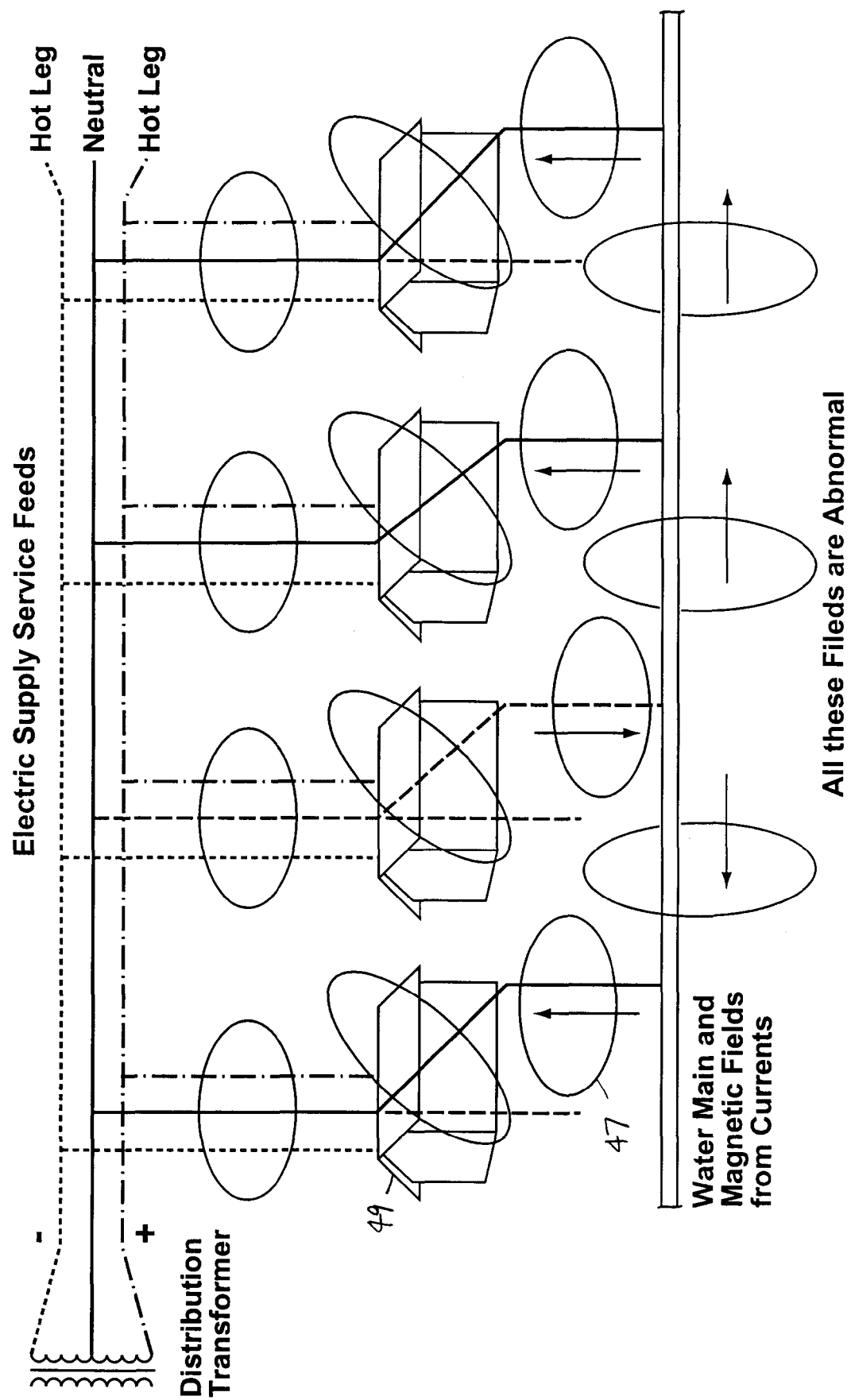
FIG. 3 (also previously described) is a schematic illustration showing abnormal electromagnetic fields generated in connection with electric supply service feeds.
Figure 4:
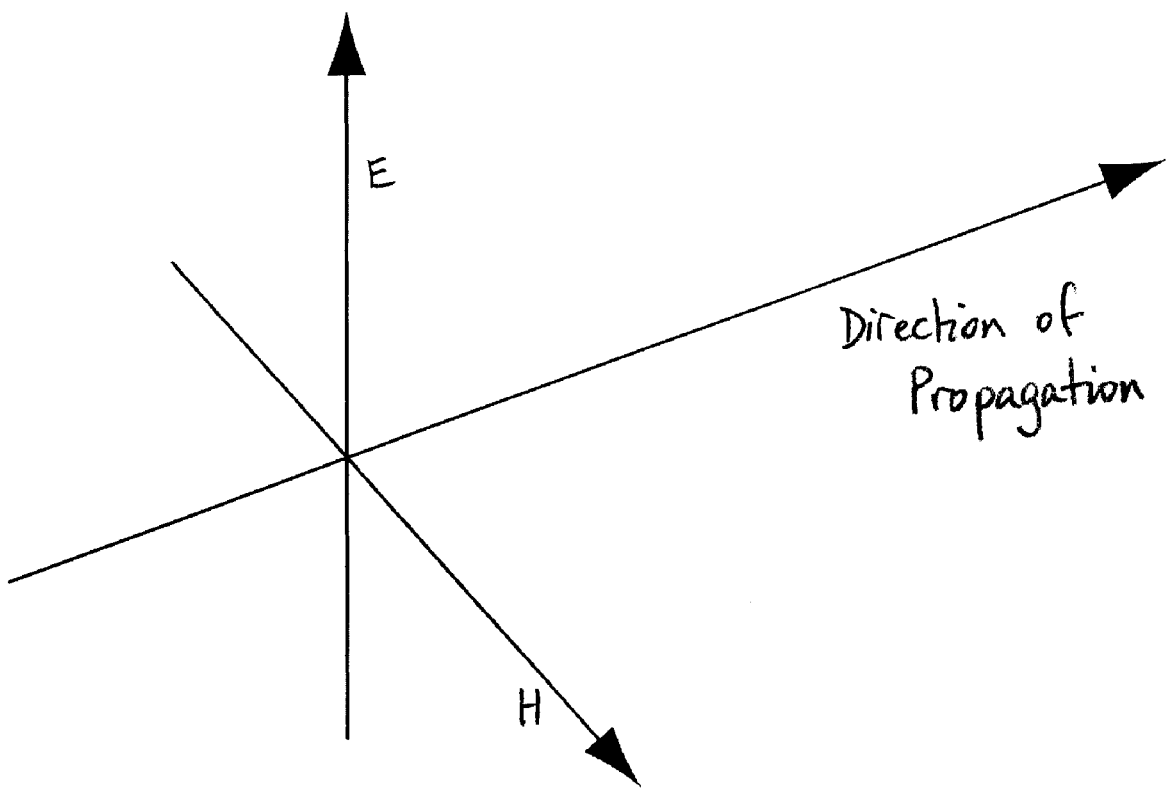
FIG. 4 (also previously described) is a schematic illustration showing electric field and magnetic field components of an electromagnetic field and a direction of propagation.
Figure 5A:
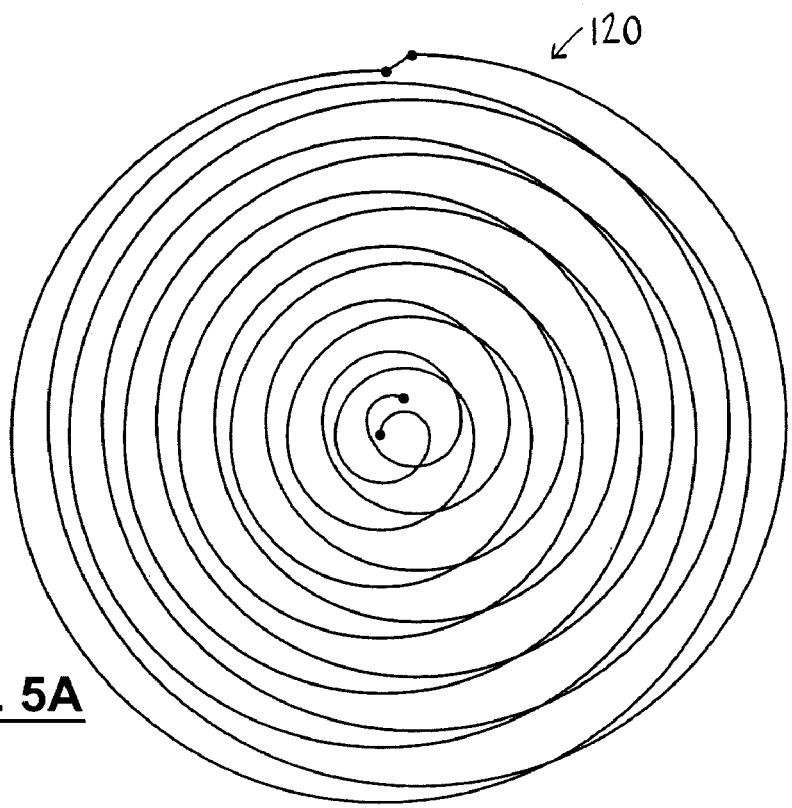
FIG. 5A is a top view of a preferred embodiment of a module of the invention.
Figure 5C:
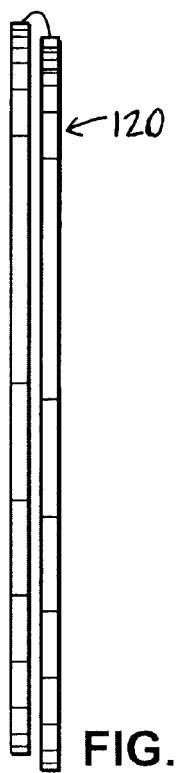
FIG. 5C is a second side view of the module of FIG. 5A.
Figure 5B:
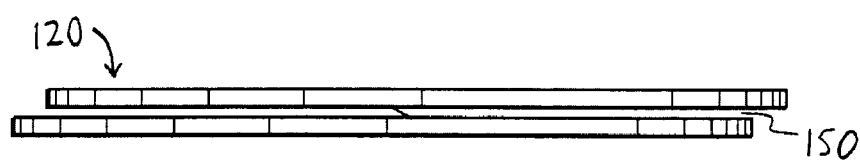
FIG. 5B is a first side view of the module of FIG. 5A.
Figure 8:
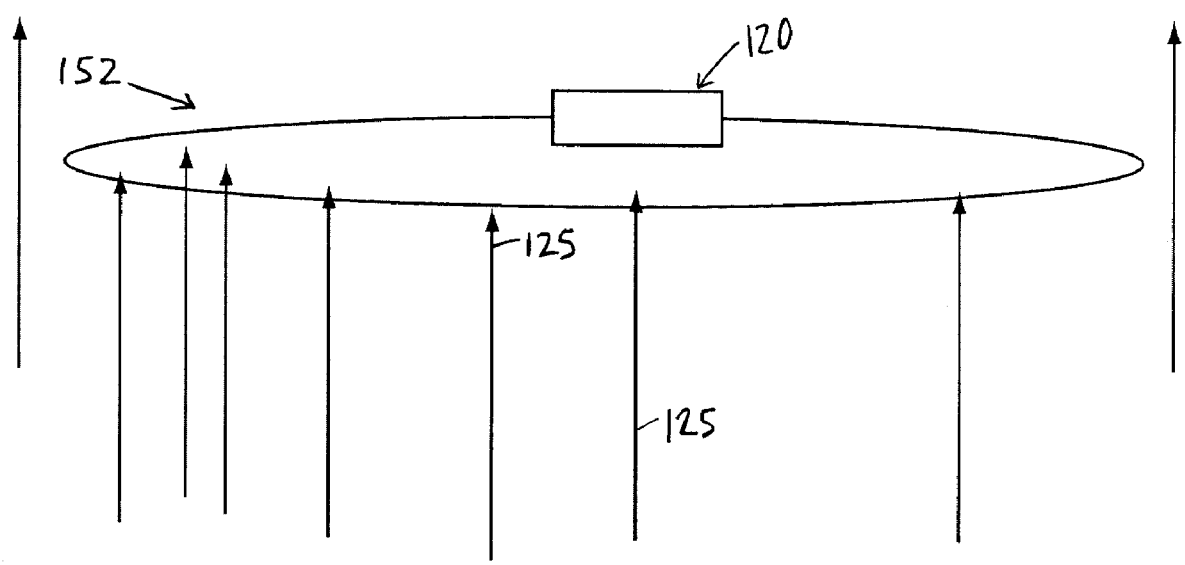
FIG. 8 is a schematic representation of a protected region in the vicinity of the module of FIG. 5A.
Figure 9:
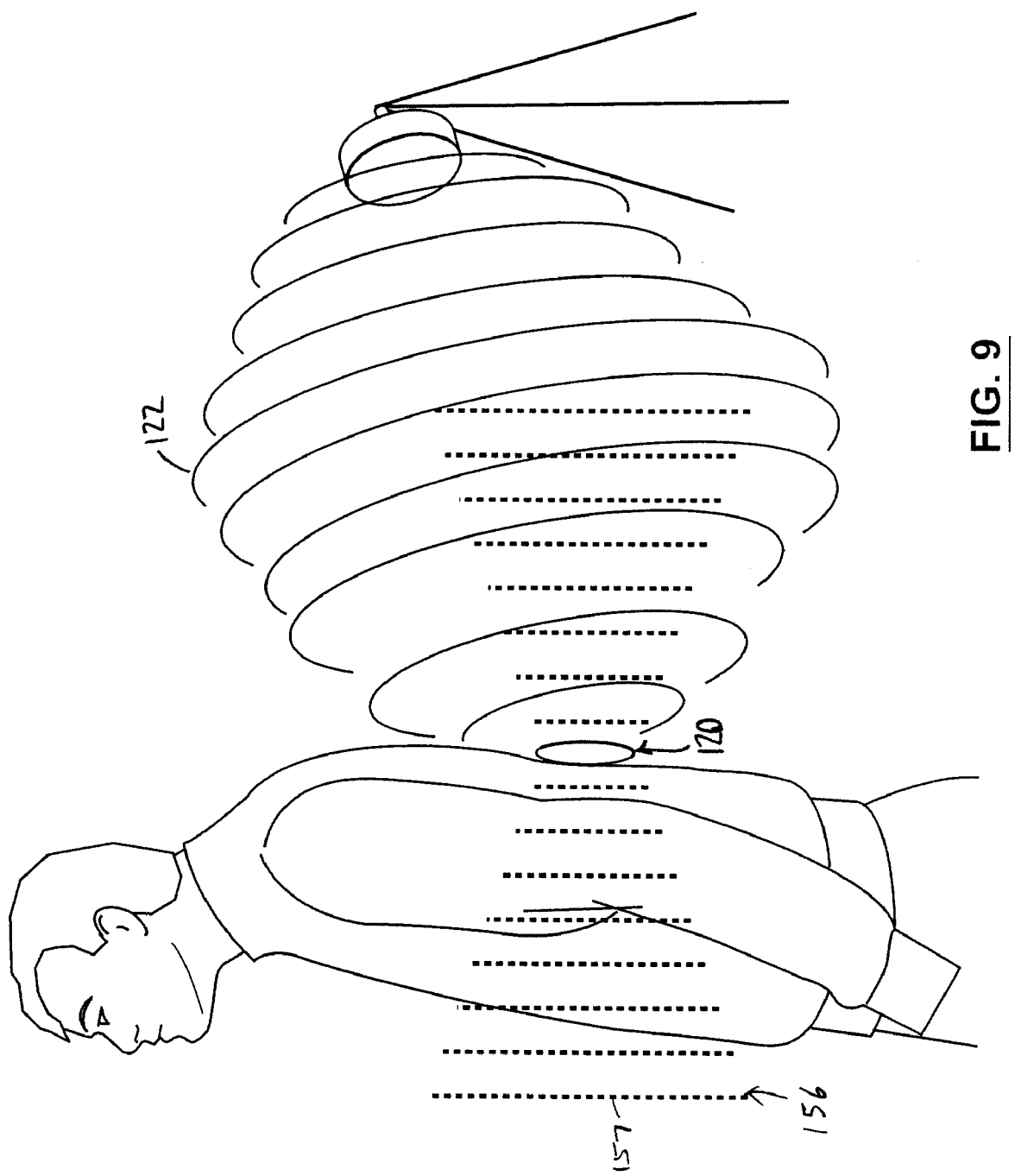
FIG. 9 is a schematic representation of the module of FIG. 5A (drawn at a smaller scale)
Figure 10:
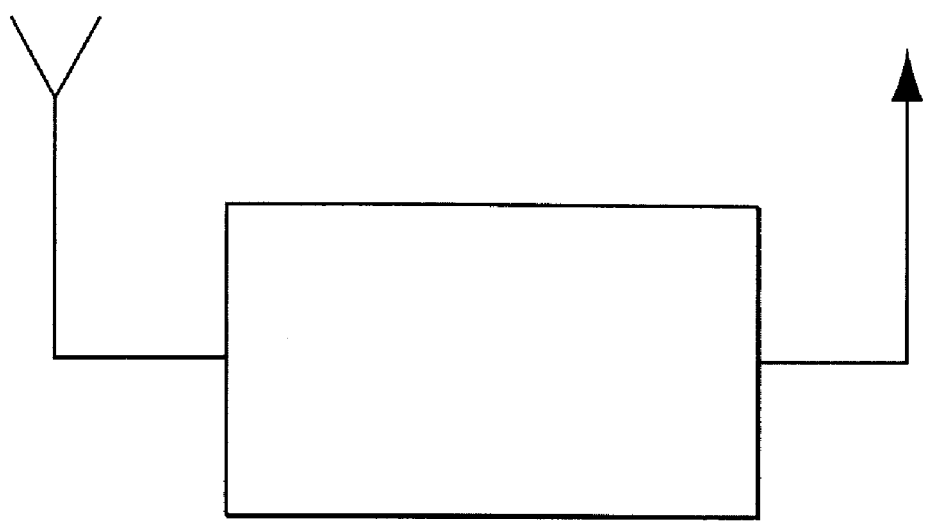
FIG. 10 is a schematic diagram representing the module of FIG. 5A.

Reference is first made to FIGS. 5A-13C to describe an embodiment of a module in accordance with the invention indicated generally by the numeral 120. The module 120 is for receiving one or more electromagnetic waves 122 moving along a path 124 in a direction of propagation (FIGS. 8, 9). The module 120 includes a first substantially electrically conductive strip 130 preferably extending between a first end 132 and a second end 134 disposed in a first pattern 136 substantially in a first plane 138 (FIG. 5B). The module 120 also includes a second substantially electrically conductive strip 140 preferably extending between a first end 142 and a second end 144 disposed in a second pattern 146 substantially in a second plane 148 (FIG. 5B). Preferably, the first and second strips 130, 140 are positioned substantially parallel to each other and spaced apart by a predetermined distance 150, and the first and second strips 130, 140 are electrically connected to each other (FIGS. 5B, 5C). As will be described, the first and second patterns 136, 146 are substantially opposite to each other, so that current (FIG. 6) passing through the first and second strips 130, 140 generates respective electromagnetic fields which are substantially opposed to each other. Preferably, the first strip is positionable in the path 124 of the electromagnetic waves 122 and substantially transverse to the direction of propagation (FIGS. 2, 8), to provide a protected region 152 from which the electromagnetic waves 122 are substantially excluded, the protected region 152 extending from the second strip 140 away from the first strip 130.

In FIG. 8, for example, the direction of propagation is schematically indicated by arrows 125.

Figure 6:
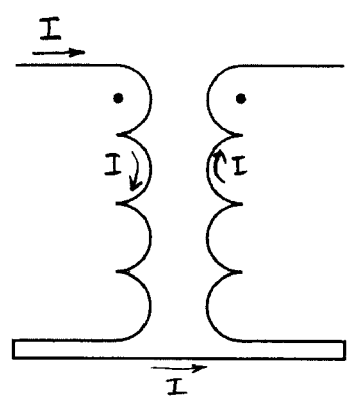
FIG. 6 is an illustration of a circuit schematically representing the module of FIG. 5A.

As shown in FIG. 6, current I flows through the first strip 130, and because the first and second strips 130, 140 are connected by a connecting portion 154, the current I also flows through the second strip 140. However, because the current I moves through the first and second strips 130, 140 in opposite directions (as shown by arrows "A" and "B" in FIG. 6), the electromagnetic fields generated by the current I are in opposition to each other. This situation is to be contrasted to the situation normally found in a transformer, in which the two windings are so positioned that current therethrough is in the same direction, i.e., electromagnetic fields generated upon current being passed through the windings work together to achieve a desired result, e.g., an increase or a decrease in voltage.

Figure 6A:
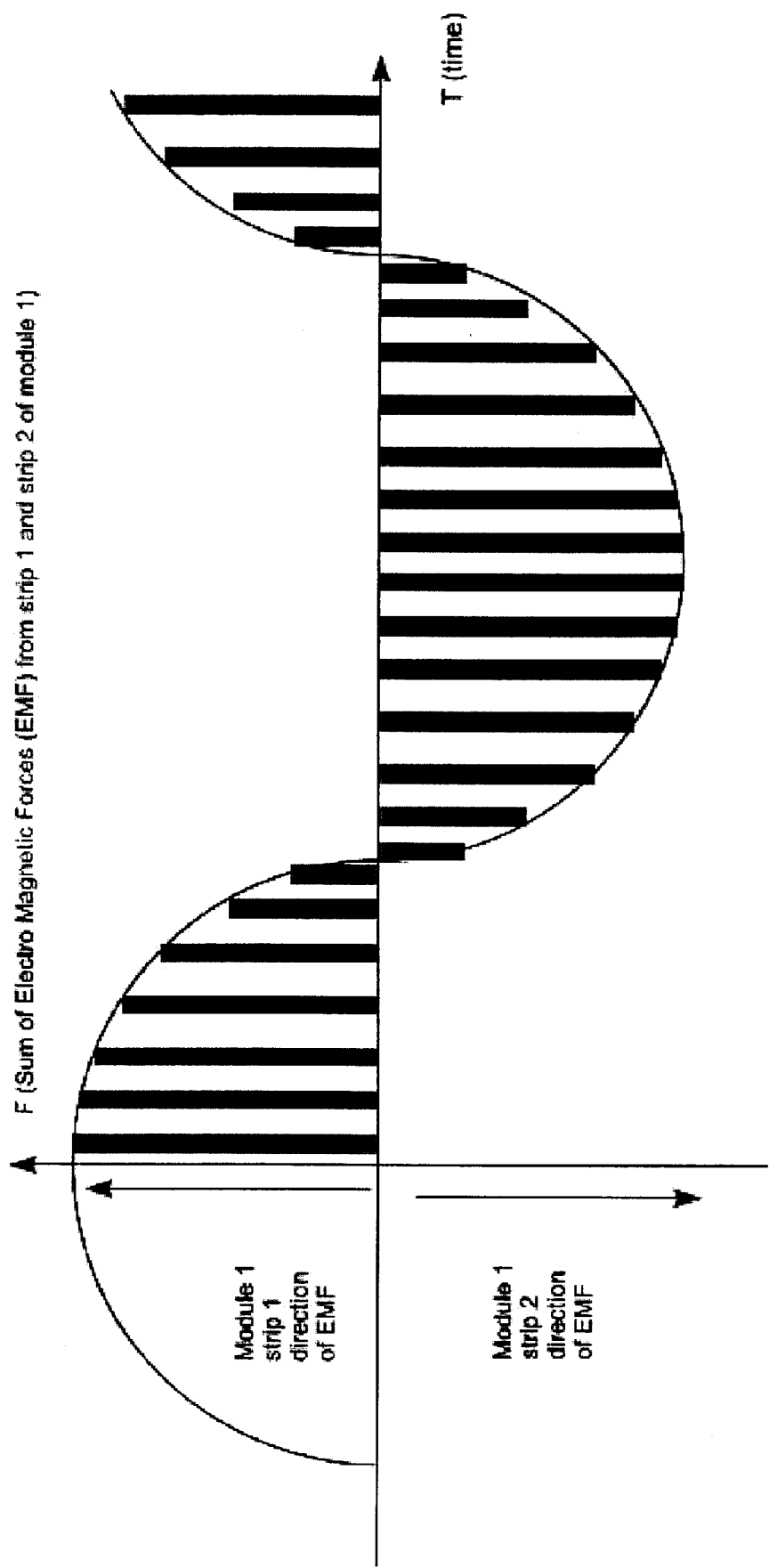
FIG. 6A is a graph representing opposing electromagnetic forces created in each module to produce one magnetic pulse.
Figure 6B:
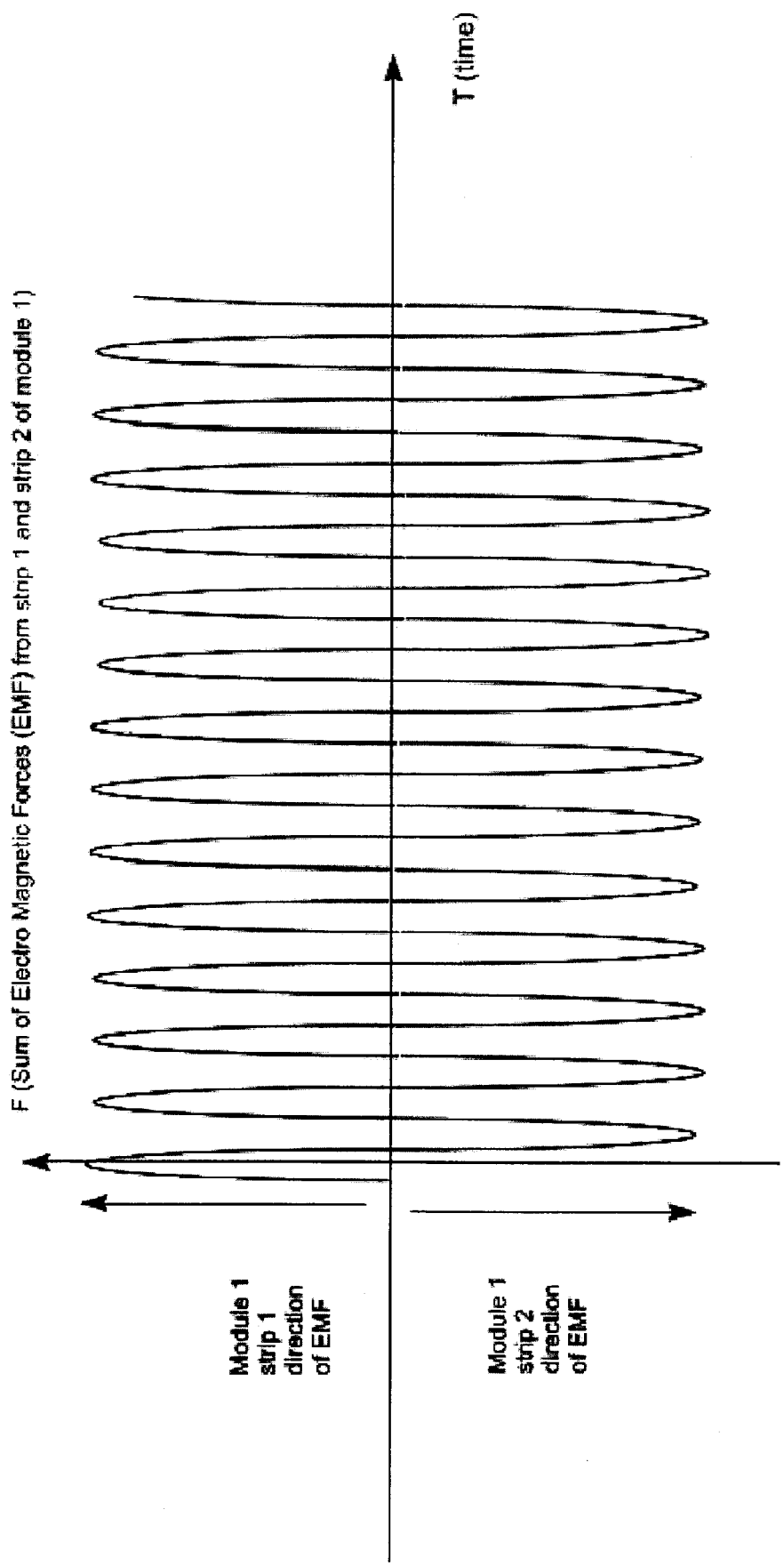
FIG. 6B is a graph representing opposing electromagnetic forces created in each module to produce a number of magnetic pulses.
Figure 7:
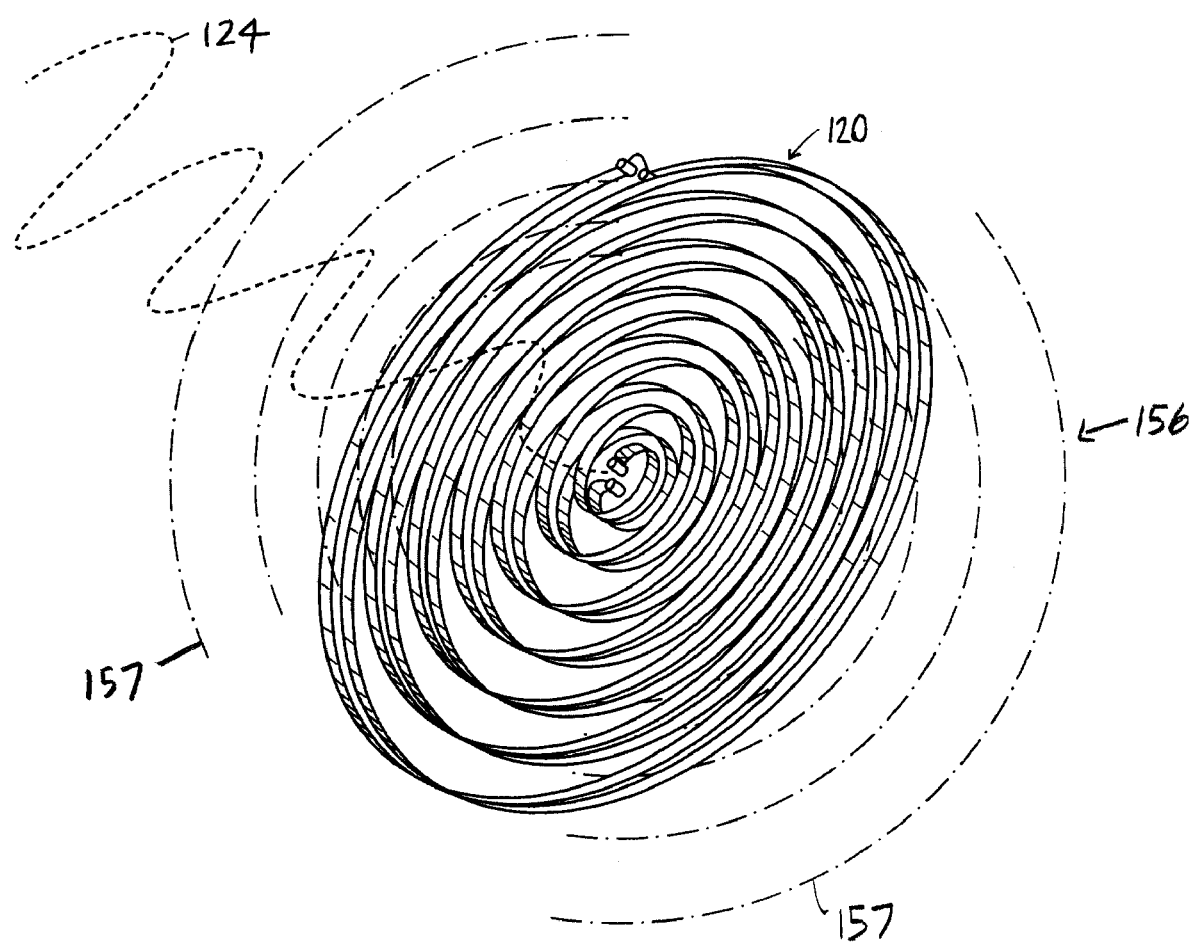
FIG. 7 is an isometric view of the module of FIG. 5A.

FIG. 6A provides a representation of the opposing electromagnetic forces produced by the electromagnetic fields created upon current I passing through the first and second strips 130, 140, for one frequency. FIG. 6A shows the electromagnetic fields when one pulse is produced. It is understood that the time differences are very small, i.e., nanoseconds. FIG. 6B provides a representation of the magnetic pulses produced by a module over a specific time period.

Preferably, current through the first and second strips 130, 140 is generated by energy in the electromagnetic waves 122. It is also preferred that one of the first and second patterns 136, 146 defines a spiral in a clockwise direction (FIG. 12A), and the other of the first and second patterns 136, 146 defines a spiral in a counterclockwise direction (FIG. 13A) so that electromagnetic fields generated by the current in the first and second strips substantially oppose each other.

In one embodiment, the first strip 130 defines a first path direction (indicated by arrow "C" in FIG. 12A) from the first end 132 to the second end 134 thereof. Also, the second strip 140 defines a second path direction (indicated by arrow "D" in FIG. 13A) from the first end 142 to the second end 144 thereof. Preferably, the first path direction and the second path direction are substantially opposite, so that electromagnetic fields generated by current in the first and second strips 130, 140 are substantially mutually opposed.

It is also preferred that the electromagnetic waves 122 are at least partially converted by the first and second strips 130, 140 into a pulsating magnetic field 156 released outwardly therefrom. The field 156 preferably includes pulses 157 which are directed substantially orthogonally to the first and second strips 130, 140 (FIG. 9).

Figure 11:
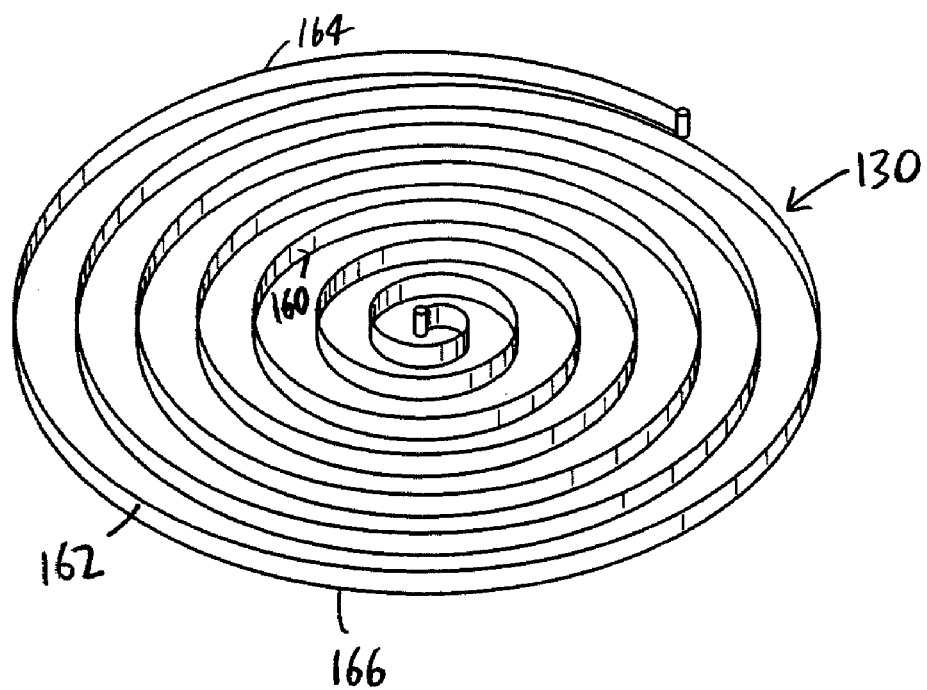
FIG. 11 is an isometric view of the first strip.

As can be seen in FIG. 11, each of the strips includes two major surfaces 160, 162 positioned between two edges 164, 166 thereof. (For convenience, only the first strip 130 is shown in FIG. 11. However, it will be understood that the second strip also has major surfaces 160, 162 between edges 164, 166.) Each of the first and second strips 160, 162 is positioned so that the major surfaces 160, 162 thereof are disposed substantially orthogonally to the first and second planes 138, 148.

The first and second strips 130, 140 may be made of any suitable substantially electrically conductive material. However, the strips preferably are made of copper. This material is preferred because it is a good conductor. Preferably, the strips 130, 140 are connected by a short strip of copper or a short piece of copper wire. It will be understood that the connection may be made anywhere which is convenient. In one embodiment, the second ends of the first and second strips are attached (as shown) due to convenience.

In one embodiment, the module 120 is preferably about 3 cm in diameter and about 0.4 cm in thickness. A module 120 having approximately these dimensions provides a protective region which is approximately large enough to accommodate at least a portion of an adult's body. It will be understood, however, that the dimensions of the module 120 may be any suitable dimensions for a particular application. It is also preferred that the module 120 is positioned inside a housing which is not generally electrically conductive, to protect the module 120. It will be understood that the housing is not shown in the drawings, for clarity. Accordingly, the module 120 preferably is provided in a very compact package which may be used in various ways, as will be described.

The mechanism pursuant to which the module provides the protected region is not well understood at this time. The following description is based on the current understanding. In use, the module 120 is exposed to one or more electromagnetic waves 122, and at least part of the energy in the electromagnetic waves 122 is converted into current through the first and second strips 130, 140. As described above, the current generates electromagnetic fields which are substantially opposed.

It also appears that the module 120 generates a substantially pulsating magnetic field. The magnetic field is generally directed away from the first and second strips 130, 140 (i.e., outwardly therefrom) and includes pulses which are directed substantially orthogonally to the first and second strips 130, 140. It is thought that the level of magnetic field is at least somewhat beneficial to the person located proximal to the module (FIG. 9). However, further research is to be done to determine the mechanism involved in the body's response to the pulsating magnetic field.

As is known, an antenna is a form of tuned circuit with inductance and capacitance. Accordingly, the circuit has a resonant frequency, i.e., a frequency at which the capacitive and inductive reactances cancel each other out. At the resonant frequency, the antenna appears to be purely resistive (i.e., the resistance being a combination of less resistance and radiation resistance).

The electromagnetic waves which are intended to be received by the device 120 have a very wide spectrum of frequencies, i.e., from less than 1 Hz to approximately 300 GHz. It appears that, in effect, in receiving the electromagnetic waves, the device 120 functions as an antenna, or more precisely, as a number of dipole antennas (or dipole antenna-like segments) having a variety of resonant frequencies.

Figure 12A:
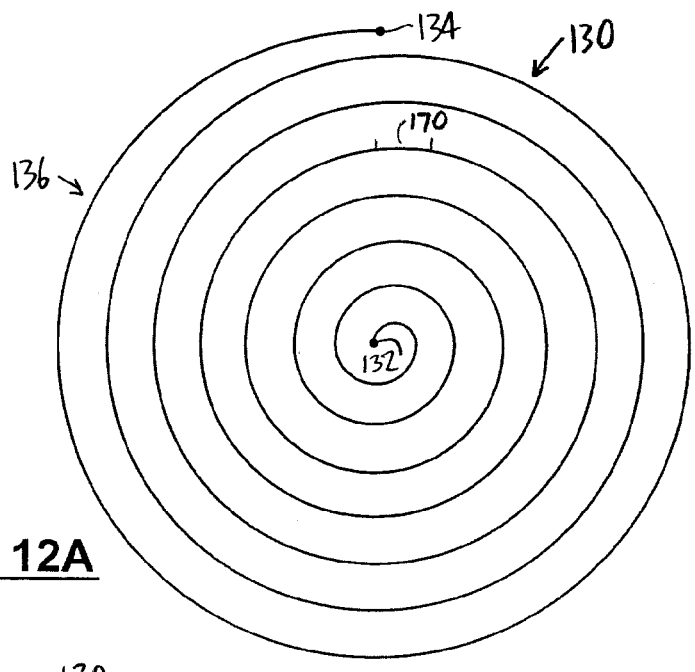
FIG. 12A is a top view of the first strip.
Figure 12C:
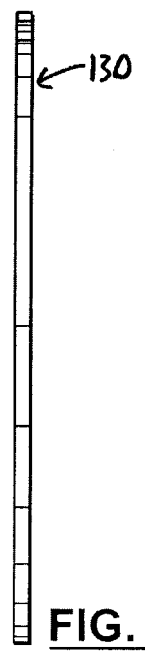
FIG. 12C is a second side view of the first strip.
Figure 12B:
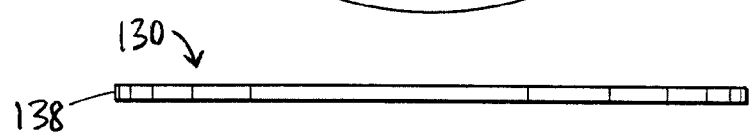
FIG. 12B is a first side view of the first strip.
Figure 13A:
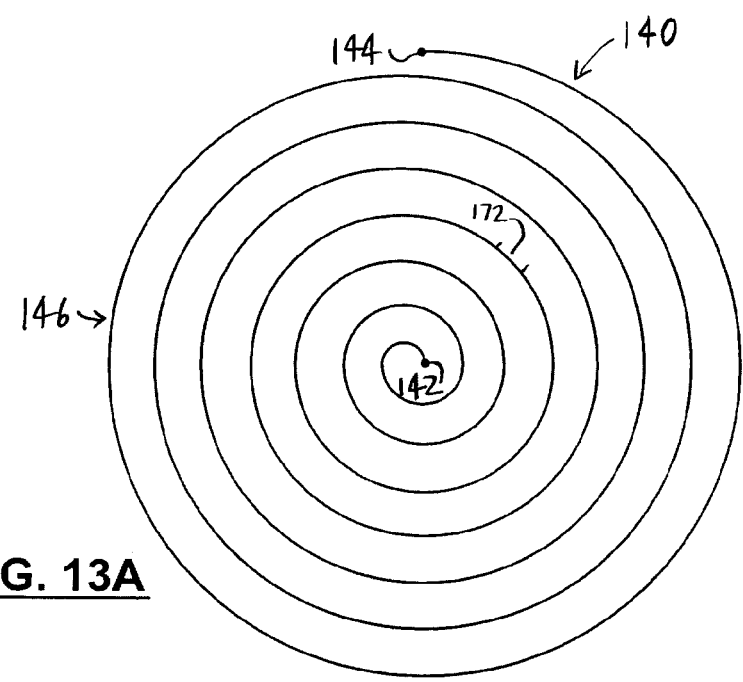
FIG. 13A is a top view of the second strip.
Figure 13C:
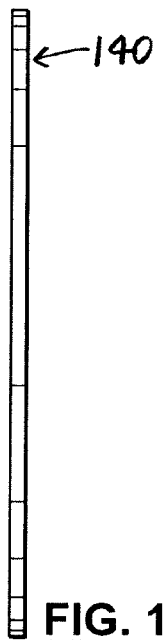
FIG. 13C is a second side view of the second strip.
Figure 13B:
FIG. 13B is a first side view of the second strip.

In the module 120, each of the first and second strips may be characterized as including a number of dipole antenna-like segments 170, 172 (FIGS. 12A and 13A). Each dipole antenna-like segment 170, 172 preferably is adapted to resonate at a predetermined frequency. Accordingly, the electromagnetic waves 122 are at least partially received at the dipole antenna-like segments 170, 172 which have resonant frequencies appropriate for the electromagnetic waves respectively. The energy in the electromagnetic waves accordingly is converted into current through the first and second strips 130, 140 which generates electromagnetic fields to provide the protected region.

Figure 14:
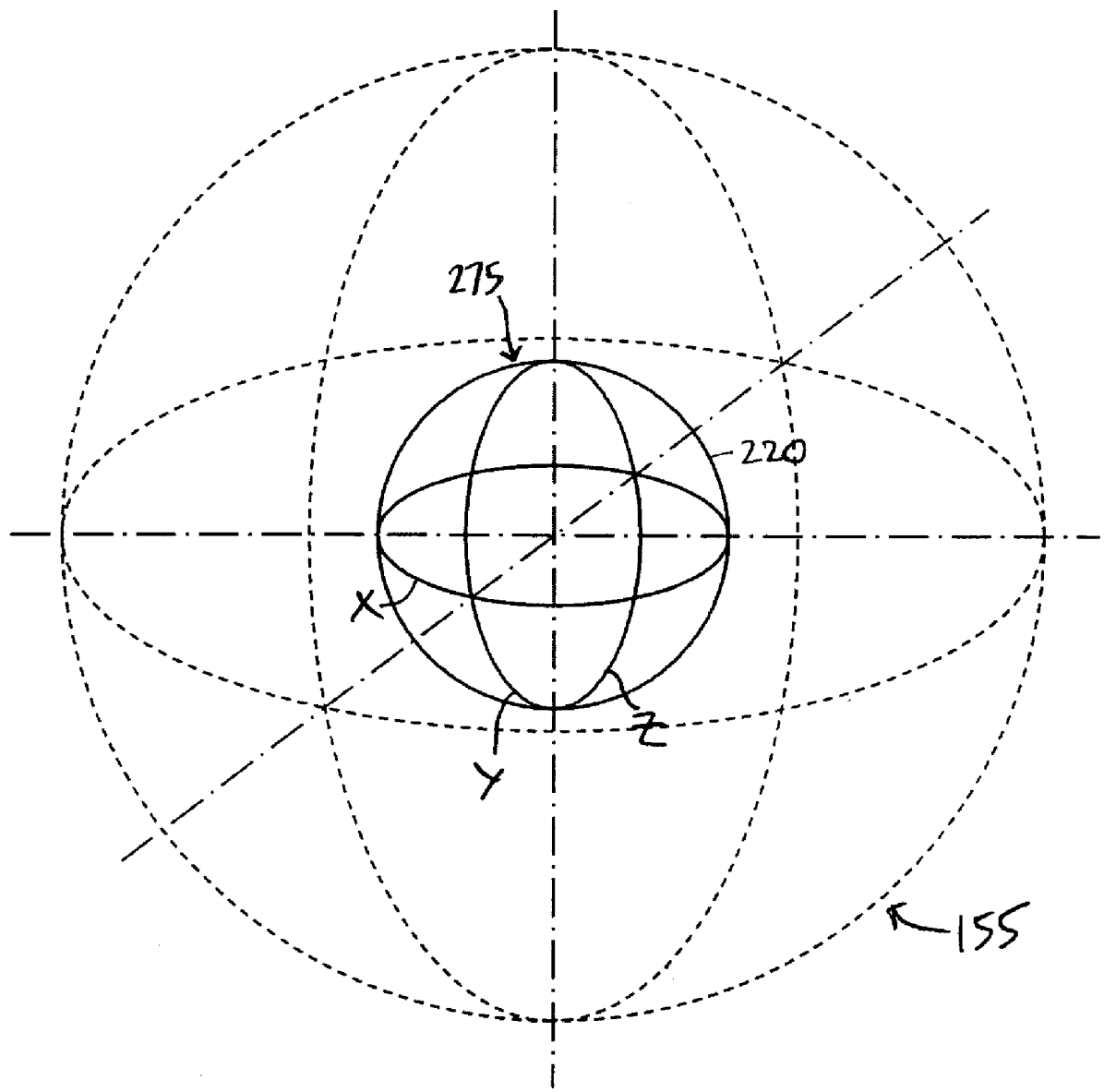
FIG. 14 is a schematic illustration of an embodiment of a system of the invention showing a substantially spherical protected region.
Figure 15:
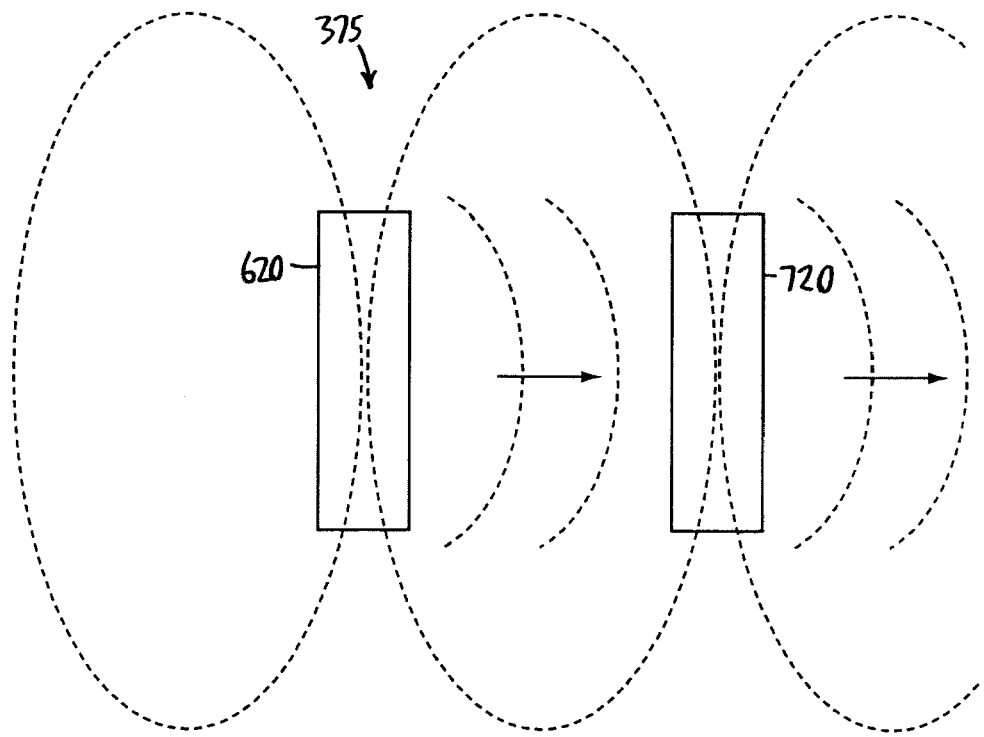
FIG. 15 is a schematic representation of an alternative embodiment of a system of the invention.
Figure 16:
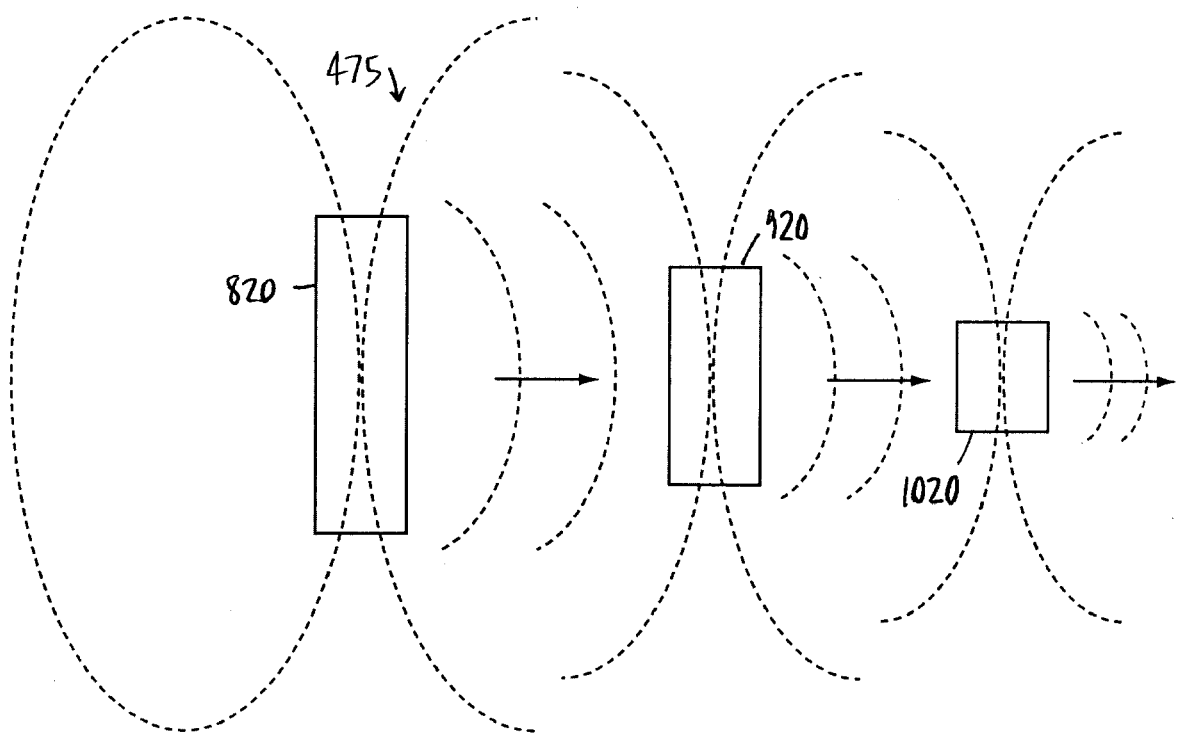
FIG. 16 is a schematic illustration of another alternative embodiment of the system of the invention.

Additional embodiments of the invention are shown in FIGS. 14-16. In FIGS. 14-16, elements are numbered so as to correspond to like elements shown in FIGS. 5A-13C.

In another embodiment, the invention provides a system 275 for receiving a number of electromagnetic waves 122 moving along paths in directions of propagation respectively. The system 275 includes two or more modules 220. Each module includes a first substantially electrically conductive strip 130 and a second substantially electrically conductive strip 140, as described above. Each of the first and second strips 130, 140 is disposed in the first and second patterns 136, 146 respectively and positioned in a first and second plane 138, 148 respectively. In all relevant respects, the modules 220 are identical to the individual module 120. In the system 275, however, each of the modules 220 is positioned substantially orthogonally to the others, for combining the protected regions 152 from which the electromagnetic waves 122 are substantially excluded to form an assembly 155 of the protected regions 152. For example, in FIG. 14, three modules 220 are shown (identified in FIG. 14 as "X", "Y", and "Z" respectively), and each is positioned orthogonally to the others. As can be seen in FIG. 14, an assembly of protected regions 152 associated with each individual module is provided. Where three modules are positioned orthogonally to each other to form a system, the assembly of protected regions is substantially spherical, as indicated in FIG. 14.

Additional embodiments of systems are shown in FIGS. 15 and 16. For example, as shown in FIG. 15, an embodiment of a system 375 includes a module 620 and a second module 720. Because the modules 620, 720 are spaced apart at an appropriate distance, the magnetic field produced by the first module (and directed to the right as shown in FIG. 15) is reinforced by the magnetic field produced by the second module and directed in the same direction. The appropriate distance preferably is the minimum distance required to electrically isolate modules 620 and 720 from each other.

Similarly, a system 475 is shown in FIG. 16 which includes modules 820, 920, and 1020. The modules 820, 920, 1020 are positioned apart respectively so that the magnetic field directed to the right (as shown in FIG. 16) is successively more concentrated as the pulses move from left to right, as shown in FIG. 16. As can also be seen in FIG. 16, the diameter of the modules is progressively smaller from left to right. The extent of the magnetic pulses provided by a module is proportional to the area of the first pattern (and the second pattern). Accordingly, the effect of the progressively smaller diameters of the modules is to concentrate the magnetic pulses produced by the modules 820, 920, and 1020 which are directed to the right (as shown in FIG. 16).

EXAMPLES

The system of the invention and the module of the invention have both been found to provide beneficial effects. The module may be used alone, and it typically is placed at or near a location on a subject's body where the discomfort or ailment appears to originate. The system may be used alone, and is typically hung from a necklace around the subject's neck. Any suitable manner of carrying the system may be used, however. The system appears to have a more generally beneficial effect on the subject's body. The system and the module may be used together.

For example, a subject suffering from low energy levels, low resistance to infection, and slow healing (i.e., of open sores) due to long-term diabetes used the modules 120 and the system 275 for two years. By the end of that period, after using one module 120 in a wristband and one module 120 in each shoe, the subject reported that he generally felt much better and had much more energy than previously. In general, the subject's condition appears to have improved gradually. The subject's blood sugar is much lower, which is very surprising in view of the subject having been diabetic for many years.

The subject had lost feeling in the soles of his feet. Modules 120 were positioned in the soles of the subject's shoes. Before the modules were put into his shoes, the subject had found walking to be increasingly difficult, even with two canes. After using the shoes with modules in them for approximately two years, the subject was able to walk using only one cane. The subject has recovered some feeling in the soles of his feet. In summary, the apparent effects of the module and the system on the subject are somewhat surprising.

In another example, a subject had severe pain in the hips, to the extent that the subject found it very difficult to walk. The cause of the pain, which became chronic, was not determined. The subject positioned one module on the subject's hip and one module in the pelvic area. The subject also used the system. After approximately one week of wearing the modules and the system, the subject had improved to the point that only a tenderness was felt in the hips. After two months of use, the subject felt sufficiently improved that the subject was able to undertake a short hike.

In yet another example, a subject had severe pain in the subject's head, on the right side. Once again, the cause of the pain was not determinable. The subject positioned the module on the subject's head, in the vicinity of the pain. The subject reported that the pain ceased shortly after the module was so positioned.

In another example, a subject who had lost a significant amount of cartilage from one of the subject's knees was in pain due to the loss of such cartilage. Two modules were positioned in an elastomeric knee band, so that the modules were located on either side of the injured knee. Within a few minutes after the knee band was positioned on the injured knee, the subject reported that the pain had decreased significantly, and was virtually gone. The subject has continued to use the knee band for over two months.

In another example, a subject suffering from eye cancer positioned a module over the affected eye every night, while sleeping. This continued for approximately nine months. It appears that, upon examination, the spread of the cancer may have stopped after the module was so used by the subject. It also appears that the cancer may have decreased somewhat in extent. However, it is understood that the growth or remission of cancer cells is not well understood, and apparently may be due to a number of factors. This example is provided only as yet another example of the apparently surprising effects which may or may not result from the use of the module and/or the system. As indicated above, the exact manner in which the surprising results appear to have been achieved has not been determined.

In the foregoing examples, the module and/or the system of the invention appear to have caused a marked improvement in an ill person's condition. The effects apparently resulting from using the module and/or the system are surprising results.

One plausible theory is that, when the module 120 and the system 275 exclude streams of electromagnetic waves from protected regions in which the subject (or part of the subject's body, as the case may be) is located, the subject's immune system is relieved of the stress imposed on it by such electromagnetic waves. When the subject's immune system is thus relieved, the immune system recovers gradually over several months, eventually becoming fully operational. As the immune system recovers, it also is able to resist, with improved effectiveness, foreign bodies or agents which may cause diseases. Ultimately, once the immune system is functioning normally, the immune system succeeds in resisting the diseases in question. However, it will be understood that the foregoing is only a plausible description of the mechanism (s) which may be operative. In any event, regardless of the mechanistic explanation, it appears that the module 120 and the system 275 has had a beneficial effect on a number of subjects.

It also appears that the pulsating magnetic field has a beneficial effect on the subject, or more precisely, on a particular part of the subject's body. However, further testing is required in order to confirm the extent of the beneficial effects of the pulsating magnetic field provided by the module and/or the system.

It will be appreciated by those skilled in the art that the invention can take many forms, and that such forms are within the scope of the invention as claimed. Therefore, the spirit and scope of the appended claims should not be limited to the descriptions of the preferred versions contained herein.

I claim:

1. A module for receiving at least one electromagnetic wave moving along a path in a direction of propagation, the module comprising:
    a first substantially electrically conductive strip extending between a first end and a second end thereof disposed in a first pattern substantially in a first plane;
    a second substantially electrically conductive strip extending between a first end and a second end thereof disposed in a second pattern substantially in a second plane;
    the first and second strips being positioned substantially parallel to each other and spaced apart by a predetermined distance, and the first and second strips being electrically connected to each other; the first and second patterns being substantially opposite to each other, such that current passing through the first and second strips generates respective electromagnetic fields which are substantially opposed to each other; and
    the first strip being positionable in the path of said at least one electromagnetic wave and substantially transverse to said direction of propagation, for providing a protected region from which said at least one electromagnetic wave is substantially excluded, said protected region extending from the second strip and substantially away from the first strip.

2. A module according to claim 1 in which said current through the first and second strips is generated by energy in said at least one electromagnetic wave.

3. A module according to claim 2 in which one of said first and second patterns defines a spiral in a clockwise direction, and the other of said first and second patterns defines a spiral in a counterclockwise direction such that electromagnetic fields generated by said current in said first and second strips substantially oppose each other.

4. A module according to claim 2 in which:
    the first strip defines a first path direction from the first end to the second end thereof;
    the second strip defines a second path direction from the first end to the second end thereof; and
    the first path direction and second path direction are substantially opposite, such that electromagnetic fields generated by said current in said first and second strips are substantially mutually opposed.

5. A module according to claim 1 in which said at least one electromagnetic wave is at least partially converted by the first and second strips into a pulsating magnetic field released outwardly therefrom and comprising pulses which are directed substantially orthogonally to the first and second strips.

6. A module according to claim 1 in which:
    each of the first strip and the second strip respectively comprises two opposed major surfaces positioned between two edges thereof; and
    each of the first strip and the second strip is positioned such that the major surfaces thereof are disposed substantially orthogonal to the first and second planes.

7. A method of receiving at least one electromagnetic wave moving along a path in a direction of propagation, said method comprising:

(a) providing a module for receiving at least one electromagnetic wave, the module comprising:
    a first substantially electrically conductive strip extending between a first end and a second end thereof disposed in a first pattern substantially in a first plane;
    a second substantially electrically conductive strip extending between a first end and a second end thereof disposed in a second pattern substantially in a second plane;
    the first and second strips being positioned substantially parallel to each other and spaced apart by a predetermined distance, and the first and second strips being electrically connected to each other; and (b) locating said module in the path of said at least one electromagnetic wave, such that the first strip is positioned substantially transverse to the direction of propagation,
    wherein said at least one electromagnetic wave is substantially obstructed from a protected region extending from the second strip and substantially away from the first strip.

8. A method according to claim 7 additionally comprising the step of:
    (a) generating a substantially pulsating magnetic field directed away from each of said first and second strips and comprising pulses directed substantially orthogonally to the said first and second strips.

9. A system for receiving a plurality of electromagnetic waves moving along paths in directions of propagation respectively, the system comprising:
    at least two modules, each said module comprising:
        a first substantially electrically conductive strip extending between a first end and a second end thereof disposed in a first pattern substantially in a first plane;
        a second substantially electrically conductive strip extending between a first end and a second end thereof disposed in a second pattern substantially in a second plane;
        the first and second strips being positioned substantially parallel to each other and spaced apart by a predetermined distance, and the first and second strips being electrically connected to each other;
        the first and second patterns being substantially opposite to each other, such that current passing through the first and second strips generate respective electromagnetic fields which are substantially opposed to each other to provide a protected region associated with the module extending from the second strip substantially away from said first strip, said electromagnetic waves being substantially excluded from said protected region; and
    each of said modules being positioned substantially orthogonally to each other, for combining the protected regions associated therewith respectively to define an assembly of protected regions from which said electromagnetic waves are substantially excluded.

10. A system according to claim 9 comprising three modules, each of the modules being positioned substantially orthogonally to the other two modules, for providing a substantially spherical assembly of protected regions from which said electromagnetic waves are substantially excluded.

11. A system according to claim 10 in which said electromagnetic waves are at least partially converted by the first and second strips in each module into a pulsating magnetic field released outwardly from said first and second strips in each said module respectively, each said pulsating magnetic field comprising pulses which are directed substantially orthogonally to the first and second strips in each module respectively.

12. A module for receiving a plurality of electromagnetic waves moving in a plurality of paths substantially in at least one direction of propagation, said electromagnetic waves having a plurality of frequencies respectively, the module comprising:
   a first substantially electrically conductive strip extending between a first end and a second end thereof disposed in a first pattern substantially in a first plane positioned substantially transverse to said at least one direction of propagation and in said paths of said electromagnetic waves;
   a second strip extending between a first end and a second end thereof disposed in a second pattern substantially in a second plane;
   the first and second strips being positioned substantially parallel to each other and spaced apart by a predetermined distance, and the first and second strips being electrically connected to each other; and
   each of the first and second strips comprising a plurality of dipole antenna-like segments, each said dipole antenna-like segment respectively being adapted to resonate at a predetermined frequency, such that said electromagnetic waves are at least partially received at said dipole antenna-like segments and converted into current through the first and second strips which generates electromagnetic fields to provide a protected region extending from the second strip substantially away from the first strip, said electromagnetic waves being substantially excluded from said protected region.

13. A module according to claim 12 in which one of said first and second patterns defines a spiral in a clockwise direction, and the other of said first and second patterns defines a spiral in a counterclockwise direction such that electromagnetic fields generated by said current in said first and second strips substantially oppose each other.

14. A module according to claim 12 in which:
   the first strip defines a first path direction from the first end to the second end thereof;
   the second strip defines a second path direction from the first end to the second end thereof; and
   the first path direction and second path direction are substantially opposite, such that electromagnetic fields generated by said current in said first and second strips are substantially mutually opposed.

15. A module according to claim 12 in which said electromagnetic waves are at least partially converted by the first and second strips into at least one pulsating magnetic field released outwardly therefrom comprising pulses which are directed substantially orthogonally to the first and second strips.

16. A module according to claim 12 in which:
   each of the first strip and the second strip respectively comprises two opposed major surfaces positioned between two edges thereof; and
   each of the first strip and the second strip is positioned such that the major surfaces thereof are disposed substantially orthogonal to the first and second planes.

17. A system for receiving a plurality of electromagnetic waves moving along respective paths in directions of propagation respectively, the system comprising:
   at least two modules, each said module comprising:
      a first substantially electrically conductive strip extending between a first end and a second end thereof disposed in a first pattern substantially in a first plane;
      a second substantially electrically conductive strip extending between a first end and a second end thereof disposed in a second pattern substantially in a second plane;
      the first and second strips being positioned substantially parallel to each other and spaced apart by a predetermined distance, and the first and second strips being electrically connected to each other;
      each of the first and second strips comprising a plurality of dipole antenna-like segments, each said dipole antenna-like segment respectively being adapted to resonate at a predetermined frequency, such that said electromagnetic waves are at least partially received at said dipole antenna-like segments and converted into current through the first and second strips which generates electromagnetic fields to provide a protected region associated with the module extending from the second strip substantially away from said first strip, said electromagnetic waves being substantially excluded from said protected region; and
   each of said modules being positioned substantially orthogonally to each other, for combining the protected regions associated therewith respectively to define an assembly of protected regions from which said electromagnetic waves are substantially excluded.

18. A system according to claim 17 comprising three modules, each of the modules being positioned substantially orthogonally to the other two modules, for providing a substantially spherical assembly of protected regions from which said electromagnetic waves are substantially excluded.

* * * * *